United States Patent [19]
Tenbrink

[11] Patent Number: 5,912,246
[45] Date of Patent: Jun. 15, 1999

[54] IMIDAZO[1,2-A]PYRIDINES FOR THE TREATMENT OF CNS AND CARDIAC DISEASES

[75] Inventor: Ruth E. Tenbrink, Richland, Mich.

[73] Assignee: Pharmacia & Upjohn Company, Kalamazoo, Mich.

[21] Appl. No.: 08/894,179

[22] PCT Filed: Feb. 12, 1996

[86] PCT No.: PCT/US96/01114

§ 371 Date: Aug. 14, 1997

§ 102(e) Date: Aug. 14, 1997

[87] PCT Pub. No.: WO96/25414

PCT Pub. Date: Aug. 22, 1996

Related U.S. Application Data

[63] Continuation of application No. 08/388,682, Feb. 15, 1995, abandoned.

[51] Int. Cl.$^6$ ............ A61K 31/495; A61K 31/435; C07D 471/04
[52] U.S. Cl. ............ 514/253; 514/228.2; 514/233.2; 514/300; 544/61; 544/121; 544/127; 544/238; 544/295; 544/357; 544/362; 546/121
[58] Field of Search ............ 544/61, 121, 238, 544/295, 357, 362; 514/253, 228.2, 233.2

[56] References Cited

U.S. PATENT DOCUMENTS

| | | | |
|---|---|---|---|
| 3,362,956 | 1/1968 | Archer | 260/268 |
| 3,381,009 | 4/1968 | Palazzo et al. | 260/268 |
| 3,472,854 | 10/1969 | Archer | 260/268 |
| 3,511,841 | 5/1970 | Archer | 260/268 |
| 3,658,822 | 4/1972 | Fauran et al. | 260/268 |
| 4,202,977 | 5/1980 | Irikura et al. | 544/362 |
| 4,910,199 | 3/1990 | Bourguignon et al. | 514/234.2 |
| 4,988,698 | 1/1991 | Kato et al. | 514/284 |

FOREIGN PATENT DOCUMENTS

| | | |
|---|---|---|
| 050563 | 4/1982 | European Pat. Off. . |
| 306408 | 9/1988 | European Pat. Off. . |
| 54039093 | 8/1977 | Japan . |
| 57-206685 | 6/1981 | Japan . |
| 92-17475-A1 | 10/1992 | WIPO . |
| 94/20497 | 9/1994 | WIPO . |
| 94/22839 | 10/1994 | WIPO . |
| 94/24105 | 10/1994 | WIPO . |

OTHER PUBLICATIONS

Derwent Abstracts 10911 K/05, for JP57–20685 (Dec. 18, 1982).

Derwent Abstracts 34368B/18, for JP54–39093 (Mar. 24, 1979).

*Primary Examiner*—Emily Bernhardt
*Attorney, Agent, or Firm*—Martha A. Gammill; Lucy X. Yang

[57] ABSTRACT

The present invention relates to imidazo[1,2-a]pyridine compounds of formula (1)

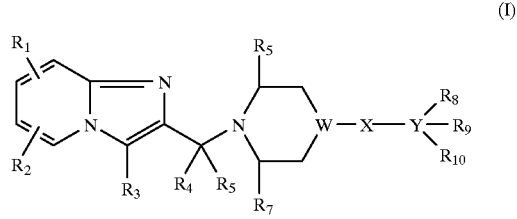

which are dopamine D-4 antagonists and useful as antipsychotic agents.

10 Claims, No Drawings

IMIDAZO[1,2-A]PYRIDINES FOR THE TREATMENT OF CNS AND CARDIAC DISEASES

This application is the national phase of international application PCT/US96/01114 which is a continuation of U.S. Ser. No. 08/388,682, filed Feb. 15, 1995, now abandoned.

FIELD OF THE INVENTION

The present invention relates to imidazo[1,2-a]pyridine compounds, which are dopamine $D_4$ antagonists, which are useful to treat and/or prevent the progression of psychotic disorders.

BACKGROUND OF THE INVENTION

Dopamine receptors mediate a number of central nervous system functions. Screening of clinical entities useful in the treatment of psychotic-like states revealed that many of the so-called "atypical" antipsychotics, which are characterized by reduced or absent extrapyramidal side effects (J. A. Lowe III, et al., Med. Res. Rev., 8, 475 (1988); M. Lader, J. Internat. Med. Res., 17, 1 (1989)), exhibit high binding affinities for the dopamine $D_4$ receptor, especially as compared to the $D_2$ receptor (Sokaloff, et al., Biochem. Pharmacol., 43, 659 (1992); Leysen, et al., Psychopharmacology, 112, S40–S54 (1993)). Seeman et al (Nature, 365, 441 (1993)) found that dopamine $D_4$ receptors are elevated 6-fold in postmortem schizophrenic brain tissue. Several other studies using positron emission tomography (Farde, et al., Arch. Gen. Psychiatry, 47, 213 (1990); Wong, et al., Science, 234, 1558 (1986) also were interpreted to indicate an increase in dopamine $D_4$ receptor levels in schizophrenics (Lahti, et al., Eur. J. Pharmacol., 236, 483 (1993)). These results support the usefulness of selective, high affinity dopamine $D_4$ antagonists for the treatment, with reduced side effects, of psychotic-like diseases (Science, 265, 1034 (1994)). See also Meth. Find. Exp. Clin. Pharmacol. 16(5): 303–307 (1994), which discloses the receptor pharmacology of a human $D_4$-dopamine receptor expressed in HEK 293 cells from a synthetic gene, which receptor should be useful for the discovery and study of novel dopamine antagonists and agonist ligands.

INFORMATION DISCLOSURE

U.S. Pat. No. 3,362,956 describes bicyclic heterocycles having fused five- and six-membered rings containing from one to three nitrogen atoms which may be in any position of the two rings (fourteen examples of such ring systems are given; none of which are imidazo[1,2-a]pyridines), linked to aryl piperazine with a carbon linker of one to, six carbons, which are useful as tranquilizers, sedatives, adrenolytic agents, hypothermic agents, anticonvulsants, hypotensive agents, and cardiovascular agents. For example, Example 21 discloses S-triazolo[4,3-a]pyridine (or pyrido[2,1-c]-s-triazole) linked to aryl piperazine with a two carbon linker at position three of the heterocycle. The heterocyles that are claimed are 3-quinoline (isoquinoline), 3,4-dihydroisoquinoline, and 1,2,3,4-tetrahydroisoquinoline. U.S. Pat. No. 3,511,841 discloses 1-[(4-, 5-, 6-, and 7-azaindolyl)-lower-alkyl]-4-substituted-piperazines which are indicated as being useful as tranquilizers, sedatives, skeletal muscle relaxants, adrenolytics, hypothermic agents, anti-convulsants, hypotensives, and cardiovascular agents.

The compounds of the present invention are imidazo[1,2-a]pyridines with a one carbon linker at position two of the heterocycle, which are useful as dopamine $D_4$ antagonists. For the present invention, it is necessary that the imidazo [1,2-a]pyridine portion of the molecule not be linked to aryl piperazine by a two carbon chain; the two carbon analog was inactive in binding to dopaminergic receptors.

WO 94/20497 discloses pyrrolo[2,3-b]pyridine derivatives, substituted at the 3-position by a substituted piperazinylmethyl moiety, which are selective dopamine $D_4$ antagonists and are expected to be of benefit in the treatment of psychotic disorders such as schizophrenia.

The compounds of the present invention are imidazo[1,2-a]pyridines substituted at the two-position by an aryl-piperazinylmethyl moiety.

WO 94/22839 discloses benzimidazole derivatives, substituted at the 2-position by a substituted piperazinylmethyl or piperazinylethyl moiety, which are selective dopamine $D_4$ antagonists and are expected to be of benefit in the treatment of pyschotic disorders such as schizophrenia.

The compounds of the present invention are imidazo[1,2-a]pyridines substituted at the two-position by an aryl-piperazinylmethyl moiety.

U.S. Pat. No. 3,472,854 discloses 1-[(1- or 2-benzimidazolyl)-lower-alkyl]4-substituted piperazines, which are useful as tranquilizers, sedatives, skeletal muscle relaxants, adrenolytics, hypothermic agents, anti-convulsants, hypotensives and cardiovascular agents. U.S. Pat. No. 3,658,822 discloses (benzimidazolyl-2-methyl)-piperazine derivatives, which exhibit cardiotropic activity, analgesic activity, sedative activity and spasmolytic activity.

The compounds of the present invention are imidazo[1,2-a]pyridines substituted at the two-position by an aryl-piperazinylmethyl moiety, which are useful as dopamine $D_4$ antagonists.

Derwent Abstracts 10911 K/05 and 34368B/18 of J 57206685 and J 54039093, respectively (as well as English translations thereof), disclose S-triazolo[1,5-a]pyridines with a carbon chain linker to aryl piperazine, in which the carbon chain may be from one to five carbons, useful for the treatment of hypertension and for treating respiratory and circulatory system diseases. U.S. Pat. No. 4,202,977 relates to S-triazolo[1,5-a]pyridines linked to aryl piperazine with a carbon chain of three or five carbons, which are useful for the treatment of hypertension.

The compounds of the present invention are imidazo[1,2-a]pyridines and the linker to the aryl piperazine is one carbon only, and active as dopamine $D_4$ antagonists.

U.S. Pat. No. 4,910,199 (English language equivalent of Eur. Pat. Appl. 306,408) discloses imidazo[1,2-b] pyridazines linked to various amines with a one-carbon chain. The amine may be, for example, an alkyl amine, morpholine, piperidine, or pyrrolidine. The compounds are useful for the treatment of cortical cholinergic deficits.

The compounds of the present invention are imidazo[1,2-a]pyridines, which when linked to piperazine must have an aryl group or an amino aryl group directly attached to the second nitrogen of the piperazine. When linked to piperidine, the piperidine must have an aryl group or an aminoaryl group attached at position four. The compounds of the present invention are also dopamine $D_4$ antagonists.

U.S. Pat. No. 4,988,698 discloses imidazo[1,2-a] pyridines with attached piperazinyl-2(1H)-quinolinones, useful for the treatment of heart diseases and hypertension, wherein the linker between the imidazo[1,2-a]pyridine and the piperazinyl-2(1H)-quinolinone is an amide or an alcohol.

The compounds of the present invention contain neither amide nor alcohol linkers nor quinolinones attached at piperazine, and are useful as dopamine $D_4$ antagonists.

U.S. Pat. No. 3,381,009 discloses triazolo[4,3-a]pyridin-3-ones connected to aryl piperazine with a three carbon linker, useful for their tranquilizing, hypotensive, and analgesic actions.

The compounds of the present invention do not contain a keto group at the three-position, are not triazolo[4,3-a] pyridines, and have only one carbon as a linker. Also they are useful as dopamine $D_4$ antagonists.

WO 92-17475-A1 discloses benzoxazoles and indazoles linked at position three with a carbon chain of one to three carbons to aryl piperazine, useful as cholinesterase inhibitors for the treatment of dementia and Alzheimer's disease and for improving memory.

The compounds of the present invention are imidazo[1,2-a]pyridines and are linked to the aryl piperazine with a one carbon chain at position two. They are also useful as dopamine $D_4$ antagonists.

WO 95/07262, published Mar. 16, 1995 (PCT filing date of Sep. 6, 1994), discloses benzo[g]indazoles which are dopamine D4 ligands and useful in the treatment of schizophrenia, depression, Parkinson's disease and tardive dyskinesias.

WO 95/29911, published Nov. 9, 1995 (Great Britain priority date of Apr. 28, 1994), discloses benzo[b]furans which are selective antagonists at the dopamine D4 receptor and useful in the treatment of schizophrenia.

WO 94/20471, published Sep. 15, 1994, discloses quinolines which bind to the D4 receptor and are useful for the treatment of psychotic disorders, particularly schizophrenia.

SUMMARY OF THE INVENTION

The present invention provides:

A compound of the formula I wherein $R_1$ and $R_2$ are the same or different and are
 a) H,
 b) fluoro,
 c) chloro,
 d) bromo,
 e) iodo,
 f) $C_1$–$C_4$ alkyl,
 g) $C_3$–$C_7$ cycloalkyl,
 h) CN,
 i) $CONR_{11}R_{12}$,
 j) $SO_2NR_{11}R_{12}$,
 k) $NR_{11}R_{12}$,
 l) $N(R_{11})SO_2R_{12}$,
 m) $N(R_{11})CO(R_{12})$,
 n) $NO_2$,
 o) OH,
 p) $O(C_1$–$C_3$ alkyl),
 q) O-phenyl,
 r) O—$CF_3$,
 s) O—$SO_2CF_3$,
 t) SH,
 u) $S(C_1$–$C_3$ alkyl),
 v) thiazolyl,
 w) imidazolyl,
 x) oxadiazolyl,
 y) aryl optionally substituted with $R_{13}$, or
 z) $CF_3$;

wherein $R_3$ is
 a) H,
 b) halo,
 c) CN,
 d) OH,
 e) $OR_4$,
 f) $(CH_2)_nOH$,
 g) $(CH_2)_nOR_4$,
 h) $(CH_2)_nOCOR_4$,
 i) $(CH_2)_nOCOOR_4$,
 j) $(CH_2)_nOCONR_{11}R_{12}$,
 k) $(CH_2)_nN(R_{11})CONR_{11}R_{12}$,
 l) $C_1$–$C_4$ alkyl,
 m) $(CH_2)_pCOOR_4$,
 n) $(CH_2)_nCONR_{11}R_{12}$,
 o) CHO, or
 p) $(CH_2)_n$—A—$(CH_2)_m$—Ar$(R_8)(R_9)(R_{10})$;
wherein A is
 a) $CH_2$,
 b) O,
 c) S, or
 d) $N(R_{11})$;
wherein $R_4$, $R_5$, $R_6$ and $R_7$ are the same or different and are
 a) H,
 b) $C_1$–$C_4$ alkyl,
 c) $C_3$–$C_7$ cycloalkyl,
 d) $C_1$–$C_3$-alkyl-$C_3$–$C_7$ cycloalkyl, or
 e) aryl optionally substituted with $R_{13}$;
wherein W is
 a) N, or
 b) CH;
wherein X is
 a) absent, or
 b) $N(R_4)$;
wherein Y is
 a) phenyl,
 b) 2-, 3- or 4-pyridinyl,
 c) 2-, 4- or 5-pyrimidinyl,
 d) 3- or 4-pyridazinyl,
 e) 2-pyrazinyl,
 f) 2-, 3-, 6- or 7-imidazo[1,2-a]pyridinyl,
 g) 2-benzoxazolyl,
 h) 2-thiobenzoxazolyl,
 i) 2-thiazolyl,
 j) 1,3-dihydro-2H-benzimidazol-2-one, or
 k) 1,3-dihydro-3-methyl-2H-benzimidazol-2-one;
wherein $R_8$, $R_9$ and $R_{10}$ are the same or different and are
 a) hydrogen,
 b) fluoro,
 c) chloro,
 d) bromo,
 e) iodo,
 f) $C_1$–$C_4$ alkyl,
 g) $C_3$–$C_7$ cycloalkyl,
 h) CN,
 i) $CONR_{11}R_{12}$
 j) $SO_2NR_{11}R_{12}$, k) $NR_{11}R_{12}$,
l) $N(R_{11})SO_2R_{12}$,
m) $N(R_{11})COR_{12}$,
n) $NO_2$,
o) OH,
p) $O(C_1–C_3\ alkyl)$,
q) O-aryl optionally substituted with $R_{13}$,
r) $O—CF_3$,
s) $O—SO_2CF_3$,
t) SH,
u) $S(C_1–C_3\ alkyl)$,
v) thiazolyl,
w) imidazolyl,
x) oxadiazolyl,
y) phenyl, or
z) 2-, 3- or 4-pyridinyl;
a1) $CF_3$,
b1) $—C(O)C_1–C_4 alkyl$,
c1) $C(O)OR_4$, or
d1) $SO_2$-phenyl optionally substituted with $R_{13}$;
wherein $R_{11}$ and $R_{12}$ are the same or different and are
  a) H,
  b) $C_1–C_4$ alkyl,
  c) $C_3–C_7$ cycloalkyl,
  d) $C_1–C_3$ alkyl-$C_3–C_7$ cycloalkyl, or
  e) aryl optionally substituted with $R_{13}$;
when $R_{11}$ and $R_{12}$ occur in $NR_{11}R_{12}$, $R_{11}$ and $R_{12}$ may be taken together with a methylene group or a heteroatom to form a five- or six-membered ring, such as piperazine, morpholine, thiomorpholine, piperidine, or pyrrolidine;
wherein aryl is
  a) phenyl,
  b) naphthyl,
  c) 2-, 3- or 4-pyridinyl, or
  d) 2-, 4- or 5-pyrimidinyl;
wherein $R_{13}$ is
  a) H,
  b) fluoro,
  c) chloro,
  d) bromo,
  e) iodo,
  f) $CH_3$,
  g) $CF_3$,
  h) CN,
  i) OH, or
  j) $OCH_3$;
wherein n is one (1) to four (4) inclusive;
wherein m is zero (0) to four (4) inclusive:
wherein p is two (2) to four (4) inclusive; and pharmaceutically acceptable salts and racemic mixtures thereof; with the following provisos:
  1) when $R_1$ or $R_2$ is $—CONR_{11}R_{12}$, then $R_{11}$ and $R_{12}$ are not both H; and
  2) when $R_8$, $R_9$ or $R_{10}$ is $—CONR_{11}R_{12}$ wherein $R_{11}$ and $R_{12}$ are both H,
then X is absent.
More particularly, the present invention provides:
The compound of the formula II wherein $R_1$ and $R_2$ are the same or different and are
  a) H,
  b) chloro,
  c) bromo,
  d) $CH_3$
  e) $O(C_1–C_2\ alkyl)$,
  f) phenyl, or
  g) $CF_3$;
wherein $R_3$ is
  a) H,
  b) $(CH_2)OH$, or
  c) $CH_2—O—CH_2$-phenyl;
wherein $R_6$ is
  a) H, or
  b) $CH_3$;
wherein W is
  a) N, or
  b) CH;
wherein Y is
  a) phenyl,
  b) 2-pyridinyl,
  c) 2-pyrimidinyl,
  d) 1,3-dihydro-2H-benzimidazol-2-one, or
  e) 1,3-dihydro-3-methyl-2H-benzimidazol-2-one;
wherein $R_8$ and $R_9$ are the same or different and are
  a) hydrogen,
  b) fluoro,
  c) chloro,
  d) CN,
  e) $CONH_2$
  f) $OCH_3$,
  g) $CF_3$,
  h) $C(O)CH_3$, or
  i) $SO_2NH_2$;
and pharmaceutically acceptable salts and racemic mixtures thereof.
Even more particularly, the present invention provides:
The compound of the formula III wherein $R_1$ and $R_2$ are the same or different and are
  a) H,
  b) chloro,
  c) bromo,
  d) $CH_3$,
  e) $OCH_3$,
  f) $OCH_2CH_3$,
  g) phenyl, or
  h) $CF_3$;
wherein $R_3$ is
  a) H,
  b) $CH_2OH$,
  c) $CH_2—O—CH_2$-phenyl;
wherein $R_6$ is
  a) H, or
  b) $CH_3$;
wherein $R_8$ and $R_9$ are the same or different and are:
  a) hydrogen,
  b) fluoro,
  c) chloro,
  d) CN,
  e) $CONH_2$, f) OCH$_3$, g) CF$_3$, h) C(O)CH$_3$, or i) SO$_2$NH$_2$;

and pharmaceutically acceptable salts and racemic mixtures thereof.

Most particularly, the present invention provides:

The compound of the formula IIIA wherein R$_1$ is a) H, b) bromo, c) chloro, or d) CH$_3$;

wherein R$_8$ and R$_9$ are the same or different and are a) H or b) chloro;

and pharmaceutically acceptable salts and racemic mixtures thereof.

Also most particularly, the present invention provides:

The compound of the formula IV wherein R$_2$ is chloro; wherein Y is a) phenyl, b) 1,3-dihydro-2H-benzimidazol-2-one, or c) 1,3-dihydro-3-methyl-2H-benzimidazol-2-one;

and pharmaceutically acceptable salts and racemic mixtures thereof;

Also, most particularly, the present invention provides:

The compound of the formula V wherein R$_2$ is chloro; wherein Y is a) 2-pyridinyl, or b) 2-pyrimidinyl;

wherein R$_8$ and R$_9$ are the same or different and are a) H, b) Cl, or c) CF$_3$;

and pharmaceutically acceptable salts and racemic mixtures thereof.

Furthermore, the present invention also provides:

A method for treating a patient having a disease associated with the dopaminergic system of the central nervous system or the heart which comprises:

administering an effective amount of a compound of formula I of claim 1.

More particularly, the present invention provides such method wherein the disease is selected from the group consisting of: schizophrenia, psychosis, depression, anxiety, drug addiction, and cardiac arrhythmias and fibrillation.

Finally, the present invention also provides:

A method for lessening the extrapyramidal motor side effects in a patient, who is being treated with an antipsychotic drug, which comprises:

administering to the patient an effective amount of a compound of formula I.

More particularly, the present invention provides such method wherein the anti-psychotic drug is selected from the group consisting of chlorpromazine, thioridazine, haloperidol, and risperidone.

Also, more particularly, the present invention provides such method wherein the dose of the anti-psychotic drug is administered at a higher dose than when the drug is administered alone.

The present invention provides compounds of the formula I and enantiomers and diastereomers thereof where such exist and pharmaceutically acceptable salts thereof to prepare a medicament to treat humans who are in need of treatment for psychosis, paraphrenia, psychotic depression, mania, dementia, schizophrenia, schizophreniform disorders, vascular headaches, migraine headaches, anxiety, drug addiction, convulsive disorders, spectrum disorders, personality disorders, attention deficit disorders in children and adults, post traumatic stress syndrome, dysthymia and extrapyramidal motor side effects of other antipsychotic (neuroleptic) drugs, such as haloperidol (see Conn's Current Therapy, R. Rakel, ed., (1994) pp. 1122–1126, Table 1).

The compounds of the present invention are named according to the IUPAC or CAS nomenclature system.

The carbon atoms content of various hydrocarbon-containing moieties is indicated by a prefix designating the minimum and maximum number of carbon atoms in the moiety, i.e., the prefix C$_i$–C$_j$ indicates a moiety of the integer "i" to the integer "j" carbon atoms, inclusive. Thus, for example, C$_1$–C$_3$ alkyl refers to alkyl of one to three carbon atoms, inclusive, or methyl, ethyl, propyl, and isopropyl, straight and branched forms thereof.

Also, the carbon atom content of various hydrocarbon-containing moieties of the present invention is indicated by a subscripted integer representing the number of carbon and hydrogen atoms in the moiety, e.g., "(CH$_2$)$_n$" indicates that the moiety "CH$_2$" is taken "n" times. Thus, for example, "(CH$_2$)$_n$"

wherein n is one to three, inclusive, represents the straight forms of methyl, ethyl and propyl.

Examples of alkyl of one to nine carbon atoms, inclusive, are methyl, ethyl, propyl, butyl, pentyl, hexyl, heptyl, octyl, and nonyl, and all isomeric forms thereof and straight and branched forms thereof.

Examples of alkenyl of one to five carbon atoms, inclusive, are ethenyl, propenyl, butenyl, pentenyl, all isomeric forms thereof, and straight and branched forms thereof.

By "halo" is meant the typical halogen atoms, such as fluorine, chlorine, bromine, and iodine.

The chemical formulas representing various compounds or molecular fragments in the specification and claims may contain variable substituents in addition to expressly defined structural features. These variable substituents are identified by a letter or a letter followed by a numerical subscript, for example, "Z" or "R$_1$" where "1" is an integer. These variable substituents are either monovalent or bivalent, that is, they represent a group attached to the formula by one or two chemical bonds. For example, a group Z would represent a bivalent variable if attached to the formula CH$_3$—C(=Z)H. Groups R$_1$ and R$_2$ would represent monovalent variable substituents if attached to the formula CH$_3$—CH$_2$—C(R$_i$)(R$_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both R$_1$ and R$_2$ are bonded to the preceding carbon atom.

Chemical formulas or portions thereof drawn in a linear fashion represent atoms in a linear chain. The symbol "—" in general represents a bond between two atoms in the chain. Thus CH$_3$—O—CH$_2$—CH(R$_1$)—CH$_3$ represents a 2-substituted-1-methoxypropane compound. In a similar fashion, the symbol "=" represents a double bond, e.g., CH$_2$=C(R$_1$)—O—CH$_3$, and the symbol "≡" represents a triple bond, e.g., HC≡C—CH(R$_1$)—CH$_2$—CH$_3$. Carbonyl groups are represented in several ways, for example: —C(O), —CO— or —C(=O)—.

The compounds of formula I of the present invention are prepared as described in the Charts, wherein the variables are as defined above or are indicated below, and Examples below, or are prepared by methods analogous thereto, which are readily known and available to one of ordinary skill in the art of organic synthesis, e.g., in PCT Application No. PCT/US94/13284, filed Nov. 30, 1994, which is incorporated by reference herein.

Chart A

Amino pyridine A-2 is prepared in several steps from pyridine A-1, which is commercially available, by the method of Lombardino, J. Med. Chem. 24:39 (1981). $R_1$ is a straight-chained or branched alkyl group.

Chart B

Bis(ethyl)amine B-b is prepared from bis amine B-a (commercially available) by treatment with an amine protecting group known to those skilled in the art, such as tert-butyloxycarbonyl or benzyloxycarbonyl. Bis(ethyl) amine B-1 is either available commercially (wherein X is Cl, Br), or from bis(ethyl)amine B-b by commonly used methods known to those skilled in the art. $R_8$ and $R_9$ are H, halo, alkyl, cycloalkyl, cyano, amino (including substituted amino), OH, O-alkyl and O-aryl. When $R_8$ and $R_9$ are strongly electron-withdrawing groups. B-3 is better made by other routes, such as those described in Chart C below or other methods known to one of ordinary skill in the art.

Aryl piperazine B-3 is prepared by heating bis(ethyl) amine B-1, wherein X is chloro, bromo, iodo, O-mesylate, or O-tosylate, in the presence of aniline B-2 with or without added base such as potassium carbonate or diisopropylethylamine, and using solvents such as DMF, THF, N,N-dimethylacetamide, or N-methyl-2-pyrrolidinone.

Chart C

Aryl piperazine C-3 is prepared by heating piperazine C-1 in the presence of fluoroaryl C-2 in solvents such as water, DMF, N-methyl-2-pyrrolidinone, THF, ethyl acetate, acetonitrile, N,N-dimethylacetamide, or dioxane, at temperatures of 80° C. to 200° C. When piperazine C-1 is used in an excess of two or more equivalents, no added base is necessary. When a single equivalent of piperazine C-1 is present, added base such as diisopropylethyl amine or potassium carbonate is used. Either $R_8$ or $R_9$ or both are electron-withdrawing groups and one of $R_8$ or $R_9$ is in either the ortho or para position relative to the fluorine atom. $R_6$ and $R_7$ are $C_1$–$C_4$ alkyl.

Chart D

Imidazopyridine D-3 is prepared from aminopyridine D-1 or the amino pyridine A-2 (refer to Chart A) and 3-halopyruvate ester D-2 (wherein halo is chloro, bromo, iodo, mesylate or tosylate) either by a two-step procedure whereby D-1 (or A-2) and D-2 are stirred in a solvent such as dimethoxyethane with or without the addition of a base such as triethylamine or potassium carbonate. The solvent is then replaced with alcoholic solvent such as methanol, ethanol, isopropanol, or tert-butanol and the mixture is heated until no additional D-3 is formed.

Alternatively, alcohol is added as a co-solvent to the mixture followed by heating until no more D-3 is formed. In some cases it is more convenient to stir D-1 and D-2 in dimethoxyethane, without added base, and collect the resulting solid D-3 and wash it with a small amount of dimethoxyethane or diethyl ether. The solid is then taken up in alcoholic solvent, and the mixture is heated until no more D-3 is formed.

Hydrolysis of D-3 with aqueous hydroxide, followed by acidification, gives carboxylic acid D-4. Carboxylic acid D-4 is condensed with aryl piperazine (refer to Chart B, B-3, and Chart C, C-3, or commercially available aryl piperazine) using a coupling reagent such as diethylcyanophosphonate, dicyclohexylcarbodiimide, carbonyl diimidazole, or ethyldimethylaminopropylcarbodiimide, to give amide D-5.

Alternatively, carboxylic acid D-4 is treated with thionyl chloride or oxalyl chloride/DMF to give an acid chloride, which is then combined with aryl piperazine to give amide D-5.

Amide D-5 is reduced to the final product, imidazopyridine alkane D-6, when $R_1$, $R_8$, and $R_9$ are non-reducible groups, with reducing agents such as lithium aluminum hydride, borane, or borane-methyl sulfide in solvents such as THF or ethyl ether. When $R_1$, $R_8$, and $R_9$ are reducible groups, the final product, D-6 is prepared by the method of Chart E, described below. $R_1$, $R_8$ and $R_9$ are, e.g., H, alkyl, halo, amino, OH, O-alkyl, $OCF_3$, $OSO_2CF_3$, SH, S-alkyl.

Chart E

Imidazopyridine salt E-3 is prepared from aminopyridine E-1 (also D-1) (refer to Chart D) (commercial source) or the amino pyridine A-2 (refer to Chart A) and dihaloacetone E-2 (Aldrich) either by a two-step procedure whereby E-1 and E-2 are stirred in a solvent such as dimethoxyethane with or without the addition of a base such as triethylamine or potassium carbonate to give imidazopyridine salt E-3. If dimethoxyethane alone is used as solvent, it is then replaced with alcoholic solvent and E-3 is heated until no additional E-4 is formed.

Alternatively, alcoholic solvent is added as a co-solvent to the dimethoxyethane mixture of E-3, followed by heating until no additional E-4 is formed.

In some cases it is more convenient to stir E-1 (or A-2) and E-2 in dimethoxyethane, without added base, and collect the resulting solid E-3 and wash it with a small amount of dimethoxyethane to remove by-products or unreacted starting material.

Imidazopyridine E-3 is then taken up in alcoholic solvent and the mixture is heated until no more haloimidazopyridine E-4 is formed. Haloimidazopyridine E-4 is then reacted with aryl piperazine B-3 (refer to Chart B) or C-3 (refer to Chart C) or commercially available aryl piperazine to give final product, imidazopyridine alkane E-5 (also D-6) (refer to Chart D). $R_1$, $R_6$, $R_7$, $R_8$ and $R_9$ are as defined above.

Chart F

Imidazopyridine carboxamide F-2 is prepared from imidazopyridine nitrile F-1 by the general method of Hall and Gisler, J. Org. Chem. 41:3769 (1976) and references cited therein, via hydrolysis of the nitrile with sodium hydroxide in tert. butanol with warming and with the addition of aq. hydrogen peroxide, to give final product, imidazopyridine carboxamide F-2. $R_1$, $R_6$, R7 and $R_8$ are as defined above, except $R_1$ and $R_8$ are not —CN.

Chart G

Imidazopyridine alkane G-1 (also D-6 and E-5 in Charts D and E above) is stirred in formalin (37% formaldehyde in water) with THF as cosolvent to give final product, imidazopyridine alcohol G-2. Imidazopyridine alcohol G-2 is reacted with a base such as sodium or potassium hydride in solvents such as THF or DMF. The resulting alkoxide intermediate is alkylated with a haloalkylaryl to give final product, imidazopyridine ether G-3. $R_1$, $R_6$, $R_7$, $R_8$ and $R_9$ are as defined above except they are not —OH or —$SO_2NH_2$.

Chart H

Final product, imidazopyridine biphenyl H-2 is prepared from imidazopyridine bromide H-1 (prepared by the method of Chart E, wherein E-1 is commercially available) by the method of Yang and Martin, Heterocycles 34:1395 (1992) and references cited therein. $R_3$, $R_6$, $R_7$, $R_8$ and $R_9$ are as defined above except they are not —Br.

Chart I

Chart I discloses a method whereby arylaminopiperidines I-5 are prepared from commercially available protected piperidinone I-1. Protected piperidinone I-1 is reacted with a substituted amine I-2 in a reductive amination in the presence of sodium cyanoborohydride in methanol or hydrogen and palladium on carbon catalyst in methanol to give the protected aminopiperidine I-3. Aminopiperidine I-3 is then reacted with an appropriate halogenated (substituted) aryl group in the presence of added base such as diisopropylethylamine or excess protected aminopiperidine I-3 to form the arylaminopiperidine I-4. The protecting group is removed by methods known to those skilled in the art, such as reacting I-4 in the presence of hydrogen with palladium catalyst to give arylaminopiperidine I-5. $R_4$ is, e.g., H or alkyl; aryl is, e.g., Ph, pyridinyl, pyrimidinyl which are not substituted with $CONH_2$.

Chart J

Chart J discloses a method of preparing arylpiperidines J-5 from commercially available protected piperidinone J-1. Protected piperidinone J-1 is reacted with a Grignard reagent (e.g., ArMgBr) by methods known to those skilled in the art to give piperidine alcohol J-2. Piperidine alcohol J-2 is then treated under dehydrating conditions such as aq. hydrochloric acid to give unsaturated piperidine J-3. The unsaturation is then removed using hydrogenation in the presence of palladium catalyst to give protected aryl piperidine J-4. The protecting group is then removed, preferably using the method of Olofson (J. Org. Chem., 49:2081 and 2795 (1984)), to give aryl piperidine J-5. Ar is, e.g., phenyl, pyridinyl or pyrimidinyl.

Chart K

Amide K-2 is prepared from amide K-1 by first treating amide K-1 (Chart E) in an aprotic solvent such as THF or DMF with a strong base such as sodium hydride, potassium hydride, potassium tert-butoxide, or LDA and then adding an alkylhalide or alkyl triflate to the mixture. $R_1$, $R_2$, $R_3$, and $R_8$ should not contain abstractable protons (and, e.g., are not $CONH_2$, $SO_2NH_2$, OH, SH). R* in K-2 is alkyl.

The imidazo[1,2-a]pyridines of formula I may contain an asymmetric center and therefore produce two enantiomers one "S" which is (−) and the other "R" which is (+). In some cases both enantiomers (+) and (−) are useful in the same way as the optically impure (racemic, ±) mixture. Hence, they may be utilized in the racemic form without separating them. However, if it is desired to utilize one of the enantiomers, the optically impure mixture can be resolved by means known to those skilled in the art. It is preferable to prepare the piperazine in chiral form or to resolve the substituted piperazine prior to its incorporation into the rest of the molecule using methods known to those skilled in the art, see for example, Optical Resolution Procedures for Chemical Compounds, Vol 1,: Amines and Related Compounds, Paul Newman, Optical Resolution Information Center, Manhattan College, Riverdale, N.Y., 10471, 1978. These optically pure compounds are then used in the same way as the racemic mixture. When used in this patent application the term "imidazo[1,2-a]pyridines" of formula I refers to and includes both enantiomers as well as optically impure forms thereof, the most common of which is a racemic mixture (±, dl).

Some imidazo[1,2-a]pyridines of formula I contain two asymmetric centers and therefore four enantiomers (SS, RR, SR, RS) exist producing two diastereomeric pairs of enantiomers, one SS,RR and the other SR,RS. The diastereomeric pairs of enantiomers can be readily separated by means known to those skilled in the art. When used in this patent application the term "imidazo[1,2-a]pyridines" of formula I includes all four enantiomers as well as optically impure forms thereof, the most common of which is a racemic mixture (±).

The imidazo[1,2-a]pyridines of formula I are bases, and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. Pharmaceutically acceptable salts refers to those salts which would be readily apparent to a manufacturing pharmaceutical chemist to be equivalent to the parent compound in properties such as formulation, stability, patient acceptance and bioavailability. The preferred pharmaceutically acceptable salts include salts of the following acids: methanesulfonic, hydrochloric (mono and di), hydrobromic, sulfuric, phosphoric, nitric, benzoic, hexamic, citric, tartaric, fumaric, maleic, $CH_3$—$(CH_2)_t$—COOH, or HOOC—$(CH_2)_t$—COOH, wherein t is 0 through 4. See P. L. Gould, "Salt Selection for Basic Drugs," International Journal of Pharmaceutics (1986), 33:201–217, see Table 1.

The compounds of the present invention may be in either free form or in protected form, as included in the claims where appropriate, at one or more of the remaining (not previously protected) carboxyl, amino, hydroxy, or other reactive groups. The protecting groups may be any of those known in the art. Examples of nitrogen and oxygen protecting groups are set forth in T. W. Greene, Protecting Groups in Organic Synthesis, Wiley, N.Y., (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (BOC), benzyloxycarbonyl, acetyl, allyl, phthalyl, benzyl, benzoyl, trityl and the like.

The compounds of the present invention being antagonists of dopamine receptor subtypes within the brain, are accordingly of benefit in the treatment and/or prevention of psychotic disorders such as schizophrenia. Thus, the compounds of this invention are useful for the treatment and/or prevention of diseases associated with the dopaminergic system of the central nervous system and the heart, for example schizophrenia, psychosis, dementia, confusional states, depression, anxiety, drug addiction, and cardiac arrhythmias and fibrillation. The compounds are also useful in combination with other drugs used in the treatment of schizophrenia and psychosis, in particular for the mitigation of motor side effects caused by these other drugs. Moreover, the compounds of the present invention have a selective affinity for the dopamine $D_4$ receptor subtype over other dopamine receptor subtypes, in particular the $D_2$ subtype, and can therefore be expected to manifest fewer or reduced side-effects than those associated with classical neuroleptic drugs.

The imidazo[1,2-a]pyridines of formula I of this invention possess selective pharmacological properties and are useful in treating humans who have a central nervous system disorders, including, for example, psychosis, paraphrenia, psychotic depression, mania, schizophrenia, and schizophreniform disorders. An amount of the imidazo[1,2-a]pyridine (I) effective to treat the central nervous system is administered to humans in need of such treatment. Other central nervous system disorders which are treated with the imidazo[1,2-a]pyridines (I) include, for example, anxiety, drug addiction, convulsive disorders, spectrum disorders, personality disorders, attention deficit disorders in children and adults, post traumatic stress syndrome and dysthymia. Additionally, the compounds are useful as cognition enhancers. With regard to schizophrenia the imidazo[1,2-a]pyridines (I) are useful to treat psychotic, affective, psychomotor and vegative symptoms of schizophrenia.

The compounds are also useful in combination with other anti-psychotic drugs such as drugs used in the treatment of schizophrenia. For examples of these other drugs, please refer to Conn's Current Therapy, R. Rakel, ed. (1994) pp. 1122–1126, Table 1, which is incorporated by reference herein. In Table 1 of the reference, chlorpromazine and thioridazine are examples of the class, phenothiazines; haloperidol is an example of the class, butyrophenones; risperidone is an example of the class, benzisoxazole. The compounds of the present invention are useful to treat the extrapyramidal motor side effects of other antipsychotic (neuroleptic) drugs. This action will allow higher doses of the latter compounds to be used and greater antipsychotic efficacy to be obtained as a result of the reduction in dose limiting side effects.

In addition to their central nervous system pharmacological activities, the compounds of this invention are also useful in treating cardiac arrhythmias and cardiac fibrillation.

In clinical practice the imidazo[1,2-a]pyridines (I) of the present invention will normally be administered orally, rectally or by injection in the form of pharmaceutical compositions containing the active ingredient either as a free base or as a pharmaceutically acceptable acid addition salt in association with one or more pharmaceutically acceptable carriers.

For therapeutic treatment of central nervous system disorders the suitable daily effective amount of the imidazo[1,2-a]pyridines (I) are from about 0.005 to about 50 mg/kg for oral application, preferably from about 0.1 to about 30 mg/kg, and from about 0.05 to about 20 mg/kg for parenteral application, preferably from about 0.1 to about 10 mg/kg. The use and administration to a patient to be treated in the clinic would be readily apparent to a person of ordinary skill in the art.

For purposes of treating cardiac arrhythmias and fibrillation the imidazo[1,2-a]pyridines (I) will normally be given orally, rectally or by injection. The daily effective amount of the imidazo[1,2-a]pyridines (I) for cardiac purposes is from about 1 to about 300 mg/kg for oral administration, preferably from about 1 to about 50 mg/kg. When given parenterally the dose is from about 0.1 to about 100 mg/kg, preferably from about 0.5 to about 50 mg/kg.

The exact dosage and frequency of administration depends on the particular imidazo[1,2-a]pyridine (I) used, the particular condition being treated, the severity of the condition being treated as well as the age, weight, and general physical condition of the particular patient, including other medication the patient may be taking. The exact dosage and frequency of administration would be well known to those skilled in the art and can be more accurately determined by measuring the blood level or concentration of the imidazo[1,2-a]pyridine (I) in the patient's blood and/or the patient's response to the particular condition being treated.

Those skilled in the art would know how to formulate the compounds of this invention into appropriate pharmaceutical dosage forms. Examples of the dosage forms include oral formulations, such as tablets or capsules, solutions or suspensions, or parenteral formulations, such as sterile solutions.

Either solid or fluid dosage forms can be prepared for oral administration. Solid compositions are prepared by mixing the compounds of this invention with conventional ingredients such as talc, magnesium stearate, dicalcium phosphate, magnesium aluminum silicate, calcium sulfate, starch, lactose, acacia, methyl cellulose, or functionally similar pharmaceutical diluents and carriers. Capsules are prepared by mixing the compounds of this invention with an inert pharmaceutical diluent and placing the mixture into an appropriately sized hard gelatin capsule. Soft gelatin capsules are prepared by machine encapsulation of a slurry of the compounds of this invention with an acceptable inert oil such as vegetable oil or light liquid petrolatum. Syrups are prepared by dissolving the compounds of this invention in an aqueous vehicle and adding sugar, aromatic flavoring agents and preservatives. Elixirs are prepared using a hydroalcoholic vehicle such as ethanol, suitable sweeteners such as sugar or saccharin and an aromatic flavoring agent. Suspensions are prepared with an aqueous vehicle and a suspending agent such as acacia, tragacanth, or methyl cellulose.

When the compounds of this invention are administered parenterally, they can be given by injection or by intravenous infusion. Parenteral solutions are prepared by dissolving the compounds of this invention in aqueous vehicle and filter sterilizing the solution before placing in a suitable sealable vial or ampule. Parenteral suspensions are prepared in substantially the same way except a sterile suspension vehicle is used and the compounds of this invention are sterilized with ethylene oxide or suitable gas before it is suspended in the vehicle.

The exact route of administration, dose, or frequency of administration would be readily determined by those skilled in the art and is dependant on the age, weight, general physical condition, or other clinical symptoms specific to the patient to be treated.

The compounds useful in this invention potently inhibit [$^3$H]-spiperone binding to human dopamine $D_4$ receptor subtypes expressed in clonal cell lines.

[$^3$H]-Spiperone Binding Studies: Competition binding experiments employ drug concentrations in duplicate. [$^3$H]-Spiperone (96Ci/mmol) is used at final concentrations of 200–800 pM. Non-specific binding (80–90% of total) is determined with 3 $\mu$M haloperidol. Binding mixtures are made in 96-deep well titer dishes (Beckman) by the addition of 50 µl of drug, 50 µl of radioligand, and 800 µl of membranes (20–60 µg protein) in binding buffer. Reactions are stopped by vacuum filtration with a Tom Tec harvester. Counting is with a 1205 Beta-plate (Wallac) using MeltiLex B/HS (Wallac) as scintillant. $IC_{50}$ values are estimated by fitting the data to a one-site model by non-linear least squares minimization. Inhibition constants ($K_i$) values are calculated with the Cheng-Prushoff equation. Further details of this assay are contained in Meth. Find. Exp. Clin. Pharmacol. 16(5):303–307 (1994), which is hereby incorporated by reference herein.

The compounds of the following examples were tested in the above assay, and all were found to possess a $K_i$ value for displacement of [$^3$H]-spiperone from the human dopamine $D_4$ receptor subtype of below 2.5 µM.

The following compounds of the present invention are preferred:
6-Chloro-2-[[4-(2,4-dichlorophenyl)-1-piperazinyl]methyl]imidazo[1,2-a]pyridine;
2-[[4-(4-Chlorophenyl)-1-piperazinyl]methyl]-8-methylimidazo[1,2-a]pyridine;
2-[[4-(2,4-Dichlorophenyl)-1-piperazinyl]methyl]-8-methylimidazo[1,2-a]pyridine monomaleic acid salt;
6-Bromo-2-[[4-(4-chlorophenyl)-1-piperazinyl]methyl]imidazo[1,2-a]pyridine; and
2-[[4-(4-Chlorophenyl)-1-piperazinyl]methyl]imidazol[1,2-a]pyridine.

The following compound of the present invention is most preferred:
6-Bromo-2-[[4-(4-chlorophenyl)-1-piperazinyl]methyl]imidazo[1,2-a]pyridine.

DESCRIPTION OF THE PREFERRED EMBODIMENTS

When the term imidazo[1,2-a]pyridines (I) is used it includes a particular compound, enantiomers thereof and racemic forms thereof where such compounds exist and are pharmacologically useful as described herein.

All temperatures are in degrees Centigrade.

TLC refers to thin-layer chromatography. $R_f$ is chromatographic movement relative to solvent front.

HPLC refers to high pressure liquid chromatography.

THF refers to tetrahydrofuran.

DMSO refers to dimethylsulfoxide.

DMF refers to dimethylformamide.

Saline refers to an aqueous saturated sodium chloride solution.

IR refers to infrared spectroscopy. Only the most intense absorptions are reported.

NMR refers to nuclear (proton) magnetic resonance spectroscopy. Chemical shifts are reported in ppm (δ) downfield from tetramethylsilane. $^1$H-NMR is proton nuclear magnetic resonance spectrum. $^{13}$C-NMR is carbon nuclear magnetic resonance spectrum.

TMS refers to trimethylsilyl.

–ϕ refers to phenyl ($C_6H_5$).

$[\alpha]_D^{25}$ refers to the angle of rotation of plant polarized light (specific optical rotation) at 25° with the sodium D line (5893A).

MS refers to mass spectrometry expressed as m/e or mass/charge unit. [M+H]$^+$ refers to the positive ion of a parent plus a hydrogen atom. EI refers to electron impact. CI refers to chemical ionization. FAB refers to fast atom bombardment. HRMS is high-resolution mass spectroscopy.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

THF is distilled from sodium or potassium metal and benzophenone prior to use. Other solvents are used as obtained from commercial suppliers.

mp are melting points and are uncorrected.

$AlCl_3$ is aluminum chloride.

Anal. is analytical data.

$CDCl_3$ is deuterio-chloroform.

$CD_3OD$ is deuterio-methanol.

$CH_2Cl_2$ is methylene chloride.

$cm^{-1}$ is reciprocal centimeters.

$CuBr_2$ is cupric bromide.

EtOAc is ethyl acetate.

$Et_3Al$ is triethyl aluminum.

HCl is hydrochloric acid.

$H_2O$ is water.

HOBT is 1-hydroxybenzotriazole hydrate.

KOH is potassium hydroxide.

M is molar (concentration).

MeOH is methanol.

$Me_2S$ is dimethyl sulfide.

mg is milligram.

$MgSO_4$ is magnesium sulfate.

mL is milliliter.

mmHg is millimeter of mercury.

N is normal (concentration).

$Na_2CO_3$ is sodium carbonate.

$Na_2SO_4$ is sodium sulfate.

Pd/C is palladium on charcoal.

TFA is trifluoroacetic acid.

The chemical structural formula for the EXAMPLEs below are set forth in Chart L and correspond to the EXAMPLEs in the following manner. E-x is the chemical structural formula for EXAMPLE x. Even though the EXAMPLE may have produced a particular salt form, the chemical structural formulas may identify the compound in its free (non-salt) form.

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques. Thus, the following Examples illustrate the present invention:

EXAMPLE 1 6-Chloro-2-[[4-(4-methoxyphenyl)-1-piperazinyl]methyl]-imidazo[1,2-a]pyridine. Refer to Chart D Step 1. Ethyl 6-Chloroimidazo[1,2-a]pyridine-2-carboxylate To 2-amino-5-chloropyridine (Aldrich; 2.19 g) in dimethoxyethane (Aldrich; 25 mL) is added ethyl 2-bromopyruvate (Aldrich; 2.37 mL). After stirring overnight, the solid is collected and washed with diethyl ether. The solid is dried under reduced pressure at 45° C. and then is partitioned between dichloromethane and aqueous sodium bicarbonate. The organic phases are dried over sodium sulfate and concentrated to give 3.05 g of ethyl 6-chloroimidazo[1,2-a]pyridine-2-carboxylate. $^1$H NMR (CDCl$_3$) δ1.44, 4.46, 7.23, 7.64, 8.16, 8.21.

Step 2. 6-Chloroimidazo[1,2-a]pyridine-2-carboxylic acid

To ethyl 6-chloroimidazo[1,2-a]pyridine-2-carboxylate (0.54 g) in ethanol (5 mL) are added 1N NaOH (3.1 mL) and water and additional ethanol to aid in stirring. After one hour, ethanol is removed under reduced pressure and the residue is acidified with 2N HCl until the pH reaches 4–6. The solid is collected and washed several times with water to give, after drying, 0.40 g of 6-chloroimidazo[1,2-a]pyridine-2-carboxylic acid. $^1$H NMR (DMSO$_{d6}$) δ7.40, 7.68, 8.44, 8.85

Step 3. 1-[(6-Chloroimidazo[1,2-a]pyridin-2-yl)carbonyl]-4-(4-methoxy-phenyl)piperazine To 6-chloroimidazo[1,2-a]pyridine-2-carboxylic acid (0.170 g) and 1-(4-methoxyphenyl)piperazine (Aldrich; 0.165 g) in dichloromethane (4 mL) are added diethyl cyanophosphonate (Aldrich; 0.157 mL) and triethylamine (0.144 mL), followed by DMF (2 mL). After stirring overnight, the mixture is quenched with aqueous sodium bicarbonate and then partitioned between dichloromethane and aqueous sodium bicarbonate. The organic layers are filtered through sodium sulfate and concentrated, and the residue is chromatographed on silica gel using methanol/dichloromethane (2/98) to give 0.212 g of 1-[(6-chloroimidazo[1,2-a]pyridin-2-yl)carbonyl]-4-(4-methoxyphenyl)piperazine; mp 180–181° C.: IR (mineral oil) 1620, 1517, 1237, 1246, 1230 cm$^{-1}$. $^1$H NMR (CDCl$_3$) δ3.16, 3.78, 3.97, 4.47, 6.86, 6.94, 7.21, 7.56, 8.10, 8.20.

Step 4. 6-Chloro-2-[[4-(4-methoxyphenyl)-1-piperazinyl]methyl]imidazo[1,2-a]pyridine To 1-[(6-chloroimidazo[1,2-a]pyridin-2-yl)carbonyl]-4-(4-methoxy-phenyl)piperazine (0.182 g) in THF (6 mL) is added borane-methyl sulfide complex (Aldrich; 0.14 mL). Additional THF (4 mL) is added and the mixture is stirred overnight, after which it is quenched with the dropwise addition of methanol. The mixture is concentrated under reduced pressure and then acetone/6N HCl (10/1) is added. The resulting mixture is stirred for 40 min and then concentrated under reduced pressure. The residue is partitioned between dichloromethane and aq. sodium bicarbonate. The organic layers are filtered through sodium sulfate, concentrated, and the residue chromatographed on silica gel using methanol/dichloromethane (2/98 to 4/96) to give 0.027 g of the title compound; mp 111–112° C.; IR (mineral oil) 1512, 1254, 1498, 1035, 830 cm$^{-1}$. $^1$H NMR (CDCl$_3$) δ2.74, 3.13, 3.76, 3.77, 6.82, 6.90, 7.12, 7.52, 7.54, 8.13.

EXAMPLE 2

4-[4-[(Imidazo[1,2-a]pyridin-2-yl)methyl]-1-piperazinyl]-benzenesulfonamide. Refer to Chart E Step 1. 2-(Chloromethyl)imidazo[1,2-a]pyridine A mixture of 2-aminopyridine (Aldrich; 0.487 g), 1,3-dichloroacetone (Aldrich; 0.73 g), and dimethoxyethane (6 mL) is stirred at room temperature for 2.5 h and then at 60° C. for 30 min. Dimethoxyethane is then removed under reduced pressure and ethanol (10 mL) is added. The mixture is stirred at 80° C. for 20 min and then cooled and concentrated under reduced pressure. The residue is partitioned between dichloromethane and aq. sodium bicarbonate and the organic layers are filtered through sodium sulfate and concentrated. Dichloromethane and ethyl acetate are added to the residue and the solids are removed by filtration. The filtrate is concentrated and the residue is chromatographed on silica gel using ethyl acetate/hexane (50/50) to give 0.495 g of 2-(chloromethyl)imidazo[1,2-a]pyridine; mp >255° C.; $^1$H NMR (CDCl$_3$) δ4.78, 6.80, 7.19 7.58, 7.62, 8.08.

Step 2. 4-(Piperazin-1-yl)benzenesulfonamide. Refer to Chart C

A mixture of 4-fluorobenzenesulfonamide (6.95 g) and piperazine (17.1 g) in 30 mL of water is heated at 100° C. overnight. The solid is then collected, washed with water and toluene, and dried under reduced pressure to give 9.2 g of 4-(piperazin-1-yl)benzenesulfonamide; mp 219–221° C.; ms m/z 241; IR (mineral oil) 1160, 822, 1332, 608, 1593, 1137 cm$^{-1}$. $^1$H NMR (DMSOd$_6$) δ2.81. 3.17 2.3 7.01. 7.07.7.61.

Step 3. 4-[4-[(Imidazo[1,2-a]pyridin-2-yl )methyl]-1-piperazinyl]-benzenesulfonamide A mixture of 2-(chloromethyl)imidazo[1,2-a]pyridine (0.495 g), 4-(piperazin-1-yl) benzenesulfonamide (0.717 g), triethylamine (0.456 mL), and ethylene glycol (6 mL) is stirred at 80° C. for 1.5 h. After cooling, water is added and the resulting solid is collected and washed with water and toluene. Chromatography on silica gel using methanol/dichloromethane (6/94) yields 0.69 g of the title compound; mp 238–242° C.; IR (mineral oil) 1150, 1152, 1331, 1308, 1508 cm$^{-1}$. $^1$H NMR (DMSOd$_6$) δ2.61. 3.28, 3.66, 6.86, 7.02, 7.06, 7.20, 7.49, 7.61, 7.85, 8.50.

EXAMPLE 3

4-[4-[(Imidazo[1,2-a]pyridin-2-yl)methyl]-1-piperazinyl]-benzamide. Refer to Chart E Step 1. 4-(Piperazin-1-yl)benzamide. Refer to Chart C A mixture of piperazine (7.56 g) and 4-fluorobenzamide (2.44 g) in water (10 mL) is heated at reflux for 27 h. The mixture is then allowed to cool slightly and the solid is collected and washed with water and dichloromethane, followed by drying to give 3.24 g of 4-(piperazin-1-yl)benzamide; mp 238–243° C.; ms m/z 205; IR (mineral oil) 1609, 1255, 1665, 1389, 3149 cm$^{-1}$. $^1$H NMR (DMSOd$_6$) δ2.59, 2.80, 3.14, 6.90, 7.02, 7.72, 7.73.

Step 2. 4-[4-[(Imidazo[1,2-a]pyridin-2-yl)methyl]-1-piperazinyl]benzamide

Following the general procedure of Example 2, Step 3, and making noncritical variations, 2-(chloromethyl)imidazo[1,2-a]pyridine (Example 2, Step 1; 0.245 g), 4-(piperazin-1-yl)benzamide (0.302 g), diisopropylethylamine (Aldrich; 0.256 mL), and ethylene glycol (2 mL) gives 0.313 g of the title compound after chromatography (silica gel, methanol/dichloromethane, 8/92, as eluent) and crystallization from methanol/dichloromethane; mp 249–250° C.; IR (mineral oil) 1608, 1398, 1253, 1739, 3133, 756 cm$^{-1}$. $^1$H NMR (CDCl$_3$) δ2.74, 3.36, 3.78, 5.7, 6.78, 6.88, 7.16, 7.55, 7.58, 7.71, 8.09.

EXAMPLE 4

4-[4-[(6-Chloroimidazo[1,2-a]pyridin-2-yl)methyl]-1-piperazinyl]benzamide. Refer to Chart E Step 1. 6-Chloro-2-(chloromethyl)imidazo[1,2-a]pyridine A mixture of 5-chloro-2-aminopyridine (Aldrich; 10.07 g), 1,3-dichloroacetone (Aldrich; 10.22 g), and dimethoxyethane (Aldrich; 35 mL) is stirred overnight, after which time ethanol (20 mL) is added and the mixture is heated at 80° C. for 7 h. After cooling, the solvents are removed under reduced pressure and the residue is partitioned between dichloromethane and aq. sodium bicarbonate. The organic layers are filtered through sodium sulfate, concentrated, and the residue chromatographed on silica gel using ethyl acetate/chloroform (5/95) to give 8.71 g of a white solid. Crystallization from dichloromethane/hexane gives 8.27 g of 6-chloro-2-(chloromethyl)imidazo[1,2-a]pyridine in two crops; mp 123–124° C.; IR (mineral oil) 1073, 800, 701, 1339, 1499, 839 cm$^{-1}$. $^1$H NMR (CDCl$_3$) δ 4.75, 7.17, 7.53, 7.60, 8.14.

Step 2. 4-[4-[(6-Chloroimidazo[1,2-a]pyridin-2-yl)methyl]-1-piperazinyl]benzamide Following the general procedure of Example 2, Step 3, and making noncritical variations, 6-chloro-2-(chloromethyl)imidazo[1,2-a]pyridine (0.500 g), 4-(piperaziny-1-yl)benzamide (Example 3, Step 1; 0.536 g), triethylamine (0.477 g), and ethylene glycol (6 mL) give 0.40 g of the title compound after chromatography on silica gel using methanol/dichloromethane (8/92) and crystallization from methanol/dichloromethane; mp 240–241° C.; IR (mineral oil) 1612, 1646, 1331, 3359, 1501 cm$^{-1}$. $^1$H NMR (DMSOd$_6$) δ2.60, 3.25, 3.66, 6.92, 7.04, 7.25, 7.54, 7.72, 7.73, 7.84, 8.80.

EXAMPLE 5

4-[4-[(6-Chloroimidazo[1,2-a]pyridin-2-yl)methyl]-1-piperazinyl]benzenesulfonamide. Refer to Chart E Following the general procedure of Example 2, Step 3, and making noncritical variations, 6-chloro-2-(chloromethyl)imidazo[1,2-a]pyridine (Example 4, Step 1; 0.500 g), 4-(piperazin-1-yl)benzenesulfonamide (Example 2, Step 2; 0.630 g), triethylamine (0.477 g), and ethylene glycol (6 mL) give 0.40 g of the title compound after chromatography on silica gel using methanol/dichloromethane (8/92) and crystallization from methanol/dichloromethane; mp 255–256° C.; IR (mineral oil) 1153, 1327, 1322, 3306, 1106 cm$^{-1}$. $^1$H NMR (DMSOd$_6$) δ2.60, 3.29, 3.66, 7.01, 7.06, 7.25, 7.54, 7.60, 7.84, 8.80.

EXAMPLE 6

2-[[4-(4-Fluorophenyl)-1-piperazinyl]methyl]-7-methylimidazol[1,2-a]pyridine. Refer to Chart E Step 1. 2-(Chloromethyl)-7-methylimidazo[1,2-α]pyridine A mixture of 2-amino-4-picoline (Aldrich; 5.00 g), 1,3-dichloroacetone (Aldrich; 5.89 g), and 1,2-dimethoxyethane (Aldrich; 44 mL) is stirred for 25 min at 53° C. at which time ethanol (47.5 mL) is added. After stirring for 2.5 h at reflux, the mixture is concentrated under reduced pressure and the residue is partitioned between dichloromethane and saturated sodium bicarbonate and brine. The organic layers are dried over MgSO$_4$ and concentrated under reduced pressure. The crude material is chromatographed on silica gel using methanol/dichloromethane (1/99 to 2/98) to give, after crystallization from dichloromethane/hexane, 3.06 g of product. A portion of this material is dissolved in dichloromethane and refluxed with activated charcoal for 30 min. The activated charcoal is removed by filtration through a pad of diatomaceous earth and the filtrate is atmospherically concentrated, at which time hexane is added. The resulting solids are filtered, washed with hexane, and vacuum dried to give 0.15 g of 2-(chloromethyl)-7-methylimidazo[1,2-α]pyridine; mp 250° C. (decomp); ms m/z 180, 182; IR (mineral oil) 774, 1649, 1504, 1252. 701 cm$^{-1}$; $^1$H NMR (CDCl$_3$) δ2.39, 4.75, 6.63, 7.32, 7.53, 7.95.

Step 2. 2-[[4-(4-Fluorophenyl)-1-piperazinyl]methyl]-7-methylimidazo[1,2-a]pyridine A mixture of 2-(chloromethyl)-7-methylimidazo[1,2-]pyridine (0.302 g), 1-(4-fluorophenyl) piperazine (Aldrich; 0.315 g), triethylamine (Aldrich; 0.26 mL), and ethylene glycol (Mallinckrodt; 2 mL) is stirred for 2 h at 80–85° C. Water (4 mL) is then added to the cooled mixture, which is then partitioned between dichloromethane and aq. sodium bicarbonate. The combined organic layers are washed with brine, dried with MgSO$_4$, and concentrated under reduced pressure. The crude material is chromatographed on silica gel using methanol/dichloromethane/ammonium hydroxide (4/96/0.5). The appropriate fractions are combined and concentrated and the resulting solid is dissolved in ethyl acetate/hexane/methanol. Activated charcoal is added and the slurry is refluxed for 30 min, at which time the activated charcoal is removed by filtration through a pad of diatomaceous earth. The filtrate is concentrated and the residue crystallized from ethyl acetate to give 0.135 g of the title compound; mp 127.5–128° C.; ms m/z 324; IR (mineral oil) 1506, 1226, 1239, 813, 1340 cm$^{-1}$; $^1$H NMR (CDCl$_3$) δ2.38, 2.74, 3.15, 3.75, 6.59, 6.89, 7.32, 7.46, 7.95.

EXAMPLE 7

4-[4-[(7-Methylimidazo[1,2-a]pyridin-2-yl)methyl]-1-piperazinyl]benzamide. Refer to Chart E A mixture of 2-(chloromethyl)-7-methylimidazo[1,2-α]pyridine (Example 6, Step 1; 0.300 g), 4-(piperazin-1-yl)benzamide (Example 3, Step 1; 0.357 g), triethylamine (Aldrich; 0.26 mL), and ethylene glycol (2 mL) is stirred for 30 min at 80–85° C. Additional ethylene glycol (1 mL) is added and the mixture is stirred for another 1.5 h. Water (8 mL) is added to the cooled mixture and the resulting solid is collected and dried. This material is adsorbed to silica gel and chromatographed on silica gel using methanol/dichloromethane/ammonium hydroxide (8/92/0.5). The appropriate fractions are combined and concentrated and the residue is crystallized from ethyl acetate/methanol to give 0.211 g of the title compound; mp 217–218° C.; ms m/z 349; IR (mineral oil) 1608, 1662, 1239, 3393, 1520 cm$^{-1}$; $^1$H NMR (CDCl$_3$) δ2.39, 2.74. 3.35. 3.75, 6.60. 6.88, 7.32, 7.46, 7.70 7.95.

EXAMPLE 8

1-[1-[(6-Chloroimidazo[1,2-a]pyridin-2-yl)methyl]-4-piperidinyl]-1,3-dihydro-2H-benzimidazol-2-one. Refer to Chart E A mixture of 6-chloro-2-(chloromethyl)imidazo[1,2-a]pyridine (Example 4, Step 1: 0.186 g), 4-(2-keto-1-benzimidazolinyl)piperidine (Aldrich; 0.201 g), triethylamine (0.094 g), and dichloromethane (4 mL) is stirred at 45° C. for 20 h, after which time the mixture is cooled. Dichloromethane and aqueous sodium bicarbonate are added and the solids collected and dried. Additional material is obtained by concentration of the organic layer. Crystallization from methanol/dichloromethane/hexane gives 0.123 g of the title compound; mp 210–211 (decomp)°C; IR (mineral oil) 1695, 1486, 1338, 736, 1074 cm$^{-1}$. $^1$H NMR (DMSOd$_6$) δ1.63, 2.19, 2.38, 3.08, 3.66, 4.12, 6.96, 7.23, 7.54, 7.87, 8.80, 10.84.

EXAMPLE 9

2-[[4-(4-Fluorophenyl)-1-piperazinyl]methyl]-6-methyl-imidazo[1,2-a]pyridine. Refer to Chart E Step 1. 2-(Chloromethyl)-6-methylimidazo[1,2-α]pyridine A mixture of 2-amino-5-picoline (Aldrich; 5.028 g), 1,3-dichloroacetone (Aldrich; 5.893 g), and 1,2- dimethoxyethane (Aldrich; 43 mL) is stirred for 1 h at 55° C., at which time ethanol (47 mL) is added and the mixture is stirred for 2.75 h at reflux. The mixture is then concentrated under reduced pressure and partitioned between dichloromethane and saturated aq. sodium bicarbonate. The combined organic layers are washed with brine, dried with $MgSO_4$, and concentrated under reduced pressure. The residue is chromatographed on silica gel using methanol/dichloromethane (1/99) and the appropriate fractions are combined and concentrated to give, after crystallization from ethyl acetate, 0.411 g of 2-(chloromethyl)-6-methylimidazo[1,2-a]pyridine. Methanol is added to the filtrate, which is then concentrated to a reduced volume. The addition of hexane gives an additional 1.50 g of 2-(chloromethyl)-6-methylimidazo[1,2-a]pyridine in two crops; mp 88–89.25° C.; ms m/z 180; IR (mineral oil) 796, 705, 699, 1343, 1510 $cm^{-1}$; $^1H$ NMR ($CDCl_3$) δ 2.32, 4.76, 7.03, 7.47, 7.53, 7.86.

Step 2. 2-[[4-(4-Fluorophenyl)-1-piperazinyl]methyl]-6-methylimidazo[1,2-a]pyridine A mixture of 2-(chloromethyl)-6-methylimidazo[1,2-a]pyridine (0.302 g), 1-(4-fluorophenyl) piperazine (Aldrich; 0.319 g), triethylamine (Aldrich; 0.26 mL), and ethylene glycol (2 mL) is stirred for 2.25 h at 80–85° C. The cooled mixture is then poured into saturated aq. sodium bicarbonate and extracted several times with dichloromethane. The combined organic layers are washed with brine, dried with $MgSO_4$, and concentrated under reduced pressure. The crude material is chromatographed on silica gel using methanol/dichloromethane/ammonium hydroxide (4/96/0.25) and crystallized from ethyl acetate/hexane to give 0.300 g of the title compound; mp 112–112.5° C.; ms m/z 324; IR (mineral oil) 1511, 804, 1234, 1246, 1345 $cm^{-1}$; $^1H$ NMR ($CDCl_3$) δ2.31, 2.74, 3.15, 3.76, 6.90, 7.46, 7.86.

EXAMPLE 10

4-[4-[(6-Methylmidazo[1,2-a]pyridin-2-yl)methyl]-1-piperazinyl]benzamide. Refer to Chart E Following the general procedure of Example 2. Step 3, and making non-critical variations, 2-(chloromethyl)-6-methylimidazo[1,2-α]pyridine (Example 9, Step 1; 0.3017 g) and 4-(piperazin-1-yl)benzamide (Example 3, Step 1; 0.3633 g) give, after chromatography on silica gel using methanol/dichloromethane/ammonium hydroxide (8/92/0.25), 0.2583 g of the title compound after crystallization from methanol/dichloromethane; mp 227–228.5° C.; MS m/z 349; IR (mineral oil) 1611, 1645, 1343, 1451, 3380 $cm^{-1}$; $^1H$ NMR ($CDCl_3$) δ2.31, 2.73, 3.35, 3.75, 6.87, 6.99, 7.46, 7.48, 7.71, 7.87.

EXAMPLE 11

6-Chloro-2-[[4-(4-fluorophenyl)-1-piperazinyl]methyl]-imidazo[1,2-a]pyridine. Refer to Chart E A mixture of 2-(chloromethyl)-6-chloroimidazo[1,2-a]pyridine (Example 4, Step 1; 0.50 g), 1-(4-fluorophenyl)piperazine (Aldrich; 0.471 g), triethylamine (0.277 g), and ethylene glycol (2 mL) is stirred at 80° C. for 1.3 h. After cooling, the mixture is partitioned between dichloromethane and aq. sodium bicarbonate. The organic layers are dried over sodium sulfate and the filtrate is concentrated under reduced pressure. The residue is chromatographed on silica gel using methanol/dichloromethane (2/98) and the appropriate fractions are combined and concentrated. The resulting material is crystallized from dichloromethane/hexane to give 0.66 g of the title compound; mp 129.5–131° C.; MS m/z at 344; IR (mineral oil) 1511, 1236, 1330, 1325, 825 $cm^{-1}$; $^1H$ NMR ($CDCl_3$) δ2.74, 3.15, 6.86–6.98, 7.13, 7.52, 7.54, 8.14.

EXAMPLE 12

6-Chloro-2-[[4-(2-chlorophenyl)-1-piperazinyl]methyl]-imidazo[1,2-a]pyridine. Refer to Chart E Following the general procedure of Example 11 and making noncritical variations, 6-chloro-2-(chloromethyl)imidazo[1,2-α]pyridine (Example 4. Step 1; 0.289 g) and 1-(2-chlorophenyl)piperazine monohydrochloride (Aldrich; 0.381 g) give, after crystallization from ethyl acetate/hexane, 0.2423 g of the title compound; mp 123–123.5° C.; MS m/z 360; IR (mineral oil) 1325, 1475, 1039, 2818, 2810 $cm^{-1}$; $^1H$ NMR ($CDCl_3$) δ2.77, 3.12, 3.79, 6.96, 7.04, 7.12, 7.21, 7.34. 7.52. 8.14.

EXAMPLE 13

2-[4-[(6-Chloroimidazo[1,2-a]pyridin-2-yl)methyl]-1-piperazinyl]benzonitrile. Refer to Chart E Following the general procedure of Example 11 and making noncritical variations, 6-chloro-2-(chloromethyl)imidazo[1,2-α]pyridine (Example 4. Step 1; 0.3373 g) and 1-(2-cyanophenyl)piperazine (Emka-Chemie; 0.347 g) give, after crystallization from dichloromethane/ethyl acetate, 0.309 g of the title compound; mp 167–169° C.; MS m/z 351, 353; IR (mineral oil) 1326, 1448, 809, 1484, 1073 $cm^{-1}$; $^1H$ NMR ($CDCl_3$) δ2.79, 3.27, 3.79, 6.99, 7.12, 7.52, 8.14.

EXAMPLE 14

1-[1-[(6-Chloroimidazo[1,2-a]pyridin-2-yl)methyl]-4-piperidinyl]-1,3-dihydro-3-methyl-2H-benzimidazol-2-one. Refer to Chart K Sodium hydride (60% in oil; 0.0071 g) is washed once with hexane and THF is added to the remaining solid. To this mixture is added 1-[1-[(6-chloroimidazo[1,2-a]pyridin-2-yl)methyl]-4-piperidinyl]-1,3-dihydro-2H-benzimidazol-2-one (Example 8; 0.052 g), followed by DMF (1 mL). After stirring for 60 min, methyl iodide (0.012 mL) is added. The mixture is stirred an additional 40 min, at which time the solvents are removed under reduced pressure and the residue is partitioned between dichloromethane and brine. The organic layers are dried over sodium sulfate and concentrated. The residue is chromatographed on silica gel using methanol/dichloromethane (4/96) and the appropriate fractions are combined and concentrated to give 0.0327 g of the title compound as a white solid; ms m/z 395; IR (mineral oil) 1700, 1498, 1340, 1714, 1074 $cm^{-1}$.

EXAMPLE 15

6-Bromo-2-[[4-(4-fluorophenyl)-1-piperazinyl]methyl]-imidazo[1,2-a]pyridine. Refer to Chart E Step 1. 6-Bromo-2-(chloromethyl)imidazo[1,2-a]pyridine A mixture of 2-amino-5-bromopyridine (Aldrich; 2.88 g), 1,3-dichloroacetone (Aldrich; 2.74 g), and dimethoxyethane (30 mL) is stirred at room temperature overnight, after which time the resulting solid is collected and washed with several milliliters of dimethoxyethane. The solid is then dissolved in ethanol and stirred at 80° C. for 5 h. After cooling, the solvent is removed under reduced pressure and the residue is partitioned between dichloromethane and aq.

sodium bicarbonate. The organic layers are dried over sodium sulfate and concentrated to give 2.43 g of material. Crystallization from dichloromethane/hexane gives 2.26 g of 6-bromo-2-(chloromethyl)imidazo[1,2-a]pyridine; mp 125–126° C.; MS m/z 244, 246; IR (mineral oil) 798, 1497, 688, 1335, 1266 cm$^{-1}$. $^1$H NMR (CDCl$_3$) δ4.75, 7.26. 7.48, 7.60, 8.24.

Step 2. 6-Bromo-2-[[4-(4-fluorophenyl)-1-piperazinyl]methyl]imidazo[1,2-a]pyridine.

Following the general procedure of Example 11 and making noncritical variations, 6-bromo-2-(chloromethyl)imidazo[1,2-a]pyridine (0.253 g), 1-(4-fluorophenyl)piperazine (Aldrich; 0.186 g), triethylamine (Aldrich; 0.104 g), and ethylene glycol (2 mL) give 0.249 g of the title compound after chromatography (silica gel, methanol/dichloromethane, 4/96) and crystallization from dichloromethane/hexane; mp 110–112° C.; MS m/z 388, 390; IR (mineral oil) 1511, 1234, 1219, 1448, 1326 cm$^{-1}$. $^1$H NMR (CDCl$_3$) δ2.74, 3.16, 3.77, 6.87–6.98, 7.21, 7.48, 7.53, 8.24.

EXAMPLE 16

4-[4-[(6-Bromoimidazo[1,2-a]pyridin-2-yl)methyl]-1-piperazinyl]benzamide. Refer to Chart E Following the general procedure of Example 2, Step 3, and making noncritical variations, 6-bromo-2-(chloromethyl)imidazo[1,2-a]pyridine (Example 15, Step 1; 0.252 g), 4-(piperazin-1-yl)benzamide (Example 3, Step 1; 0.211 g), triethylamine (0.104 g), and ethylene glycol (2 mL) give 0.206 g of the title compound after crystallization from methanol/dichloromethane/hexane; mp 238–239° C.; MS m/z 413,415; IR (mineral oil) 1612, 1656, 3379, 1331, 1240 cm$^{-1}$. $^1$H NMR (DMSO-d$_6$) δ2.60, 3.25, 3.66, 6.92, 7.04, 7.32, 7.49, 7.71, 7.73, 7.83, 8.87.

EXAMPLE 17

6-Chloro-2-[[4-(4-chlorophenyl)-1-piperazinyl]methyl]-imidazo[1,2-a]pyridine. Refer to Chart E Following the general procedure of Example 11 and making noncritical variations, 6-chloro-2-(chloromethyl)imidazo[1,2-a]pyridine (Example 4, Step 1; 0.354 g), 1-(4-chlorophenyl)piperazine dihydrochloride (Aldrich; 0.475 g), triethylamine (0.552 g), and ethylene glycol (2 mL) give 0.363 g of the title compound after chromatography (silica gel, methanol/dichloromethane, 4/96) and crystallization from dichloromethane/hexane; mp 145–146° C.; MS m/z 360; IR (mineral oil) 823, 1500, 1496, 1225, 814 cm$^{-1}$. $^1$H NMR (CDCl$_3$) δ2.72, 3.19, 3.76, 6.83, 7.13, 7.19, 7.52, 7.53, 8.14.

EXAMPLE 18

6-Chloro-2-[[4-(3-chlorophenyl)-1-piperazinyl]methyl]-imidazo[1,2-a]pyridine. Refer to Chart E Following the general procedure of Example 11 and making noncritical variations, 6-chloro-2-(chloromethyl)imidazo[1,2-a]pyridine (Example 4, Step 1; 0.354 g), 1-(3-chlorophenyl)piperazine dihydrochloride (Aldrich; 0.475 g), triethylamine (0.552 g), and ethylene glycol (2 mL) give 0.372 g of the title compound after chromatography (silica gel, methanol/dichloromethane, 4/96) and crystallization from dichloromethane/hexane; mp 148–149° C.; MS m/z 360; IR (mineral oil) 1594, 1340, 1073, 1218, 1502 cm$^{-1}$. $^1$H NMR (CDCl$_3$) δ2.71, 3.23, 3.76, 6.79, 6.86, 7.14, 7.52, 7.53, 8.14.

EXAMPLE 19

6,8-Dichloro-2-[[4-(4-fluorophenyl)-1-piperazinyl]methyl]-imidazo[1,2-a]pyridine. Refer to Chart E Step 1. 6,8-Dichloro-2-(chloromethyl)imidazo[1,2-α]pyridine A mixture of 2-amino-3,5-dichloropyridine (Aldrich; 5.12 g), 1,3-dichloroacetone (Aldrich; 4.68 g), and dimethoxyethane (28 mL) is stirred overnight at room temperature. Ethanol (28 mL) is then added and the mixture is refluxed for 7.5 h and then stirred overnight at room temperature. The mixture is then refluxed for an additional 24 h and is then concentrated under reduced pressure and partitioned between saturated aq. sodium bicarbonate and dichloromethane. The combined organic layers are washed with brine, dried with MgSO$_4$, and concentrated under reduced pressure. The residue is adsorbed to silica gel and chromatographed on silica gel using ethyl acetate/chloroform (10/90), followed by a second chromatography of the combined product fractions using methanol/dichlormethane (2/98), to give 2.22 g of 6,8-dichloro-2-(chloromethyl)imidazo[1,2-α]pyridine in three crops after crystallization from methanol/dichloromethane; mp 162–163° C.; MS m/z 234, 236, 238; IR (mineral oil) 994, 808, 861, 1522, 3056 cm$^{-1}$; $^1$H NMR (CDCl$_3$) δ4.79, 7.69, 8.10.

Step 2. 6,8-Dichloro-2-[[4-(4-fluorophenyl)-1-piperazinyl]methyl]imidazo[1,2-a]pyridine A mixture of 6,8-dichloro-2-(chloromethyl)imidazo[1,2-α]pyridine (0.3064 g), 1-(4-fluorophenyl)piperazine (Aldrich; 0.266 g), triethylamine (Aldrich; 0.21 mL), and ethylene glycol (2 mL) is stirred for 1 h at 80–85° C. After cooling, the mixture is partitioned between water and dichloromethane and the organic layers are washed with brine and dried over MgSO$_4$. After concentration under reduced pressure, the residue is chromatographed on silica gel using methanol/dichloromethane (4/96) and the appropriate fractions are combined and concentrated and the residue is crystallized from ethyl acetate/hexane to give 0.3098 g of the title compound; mp 126.5–127.5° C.; MS m/z 378, 380; IR (mineral oil) 1510, 1215, 1335, 826, 1224 cm$^{-1}$; $^1$H NMR (CDCl$_3$) δ2.75, 3.15, 3.83, 6.87, 6.96, 7.26, 7.62, 8.09.

EXAMPLE 20

2-[4-[(6-Chloroimidazo[1,2-a]pyridin-2-yl)methyl]-1-piperazinyl]benzamide. Refer to Chart E Step 1. 2-(Piperazin-1-yl)benzamide. Refer to Chart C A mixture of 2-fluorobenzamide (Aldrich; 9.83 g), piperazine (Aldrich; 30.5 g), and water (135 mL) is heated at 100° C. for 26 h and at room temperature for an additional 3 days. About two-thirds of the water is then distilled off and the mixture is heated again at 100° C. overnight. After cooling, the resulting solid is collected, washed with water and toluene, and dried under reduced pressure to give 2.42 g of 2-(piperaziny-1-yl)benzamide: mp 128–134° C.; ms m/z 205; IR (mineral oil) 3322, 3274, 1595, 1665, 2815 cm$^{-1}$; $^1$H NMR (CDCl$_3$) δ2.36, 3.02, 5.91, 7.23, 7.48, 8.16, 9.55.

Step 2. 2-[4-[(6-Chloroimidazo[1,2-a]pyridin-2-yl)methyl]-1-piperazinyl]benzamide Following the general procedure of Example 11 and making non-critical variations, 6-chloro-2-(chloromethyl)imidazo[1,2-α]pyridine (Example 4, Step 1; 0.306 g) and 2-(piperazin-1-yl)benzamide (0.336 g) are converted to 0.236 g of the title compound after chromatography on silica gel using methanol/dichloromethane (8/92) and crystallization from ethyl acetate/dichloromethane. A portion of this material was recrystallized from ethyl acetate/methanol/hexane; mp 178–179° C.; ms m/z 369; IR (mineral oil) 1663, 3289, 1325, 1448, 796 cm$^{-1}$; $^1$H NMR (CDCl$_3$) δ2.75, 3.08, 3.78, 5.76, 7.13, 7.23, 7.46, 7.52, 7.53, 8.14, 8.17, 9.57.

EXAMPLE 21

2-[4-[(6-Chloroimidazo[1,2-a]pyridin-2-yl)methyl]-1-piperazinyl]-5-fluorobenzonitrile. Refer to Chart E Step 1. 5-Fluoro-2-(piperazin-1-yl)benzonitrile. Refer to Chart C A mixture of piperazine (Aldrich; 1.28 g), 2,5-difluorobenzonitrile (Lancaster; 0.422 g), and DMF (4 mL) is stirred at 80° C. for 1.5 h, after which the mixture is cooled and partitioned between dichloromethane, water, and aq. sodium bicarbonate. The organic layers are dried over sodium sulfate, concentrated, and the residue is crystallized from dichloromethane/ethyl ether/hexane to give 0.282 g of 5-fluoro-2-(piperazin-1-yl)benzonitrile; mp 83–83.5° C.; $^1$H NMR (CDCl$_3$) δ3.10, 7.00, 7.21, 7.27.

Step 2. 2-[4-[(6-Chloroimidazo[1,2-a]pyridin-2-yl)methyl]-1-piperazinyl]-5-fluorobenzonitrile Following the general procedure of Example 11 and making noncritical variations, 6-chloro-2-(chloromethyl)imidazo[1,2-a]pyridine (Example 4, Step 1; 0.199 g), 5-fluoro-2-(piperazin-1-yl)benzonitrile (0.203 g), triethylamine (0.110 g), and ethylene glycol (2 mL) give 0.218 g of the title compound after chromatography (silica gel, methanol/dichloromethane, 4/96) and crystallization from dichloromethane/hexane; mp 179–180° C.; MS m/z 369; IR (mineral oil) 1494, 1329, 808, 1452, 1072 cm$^{-1}$. $^1$H NMR (CDCl$_3$) δ2.78, 3.20, 3.78, 6.99, 7.13, 7.19, 7.26, 7.51, 7.52.8.14.

EXAMPLE 22

4-[4-[(6,8-Dichloroimidazo[1,2-a]pyridin-2-yl)methyl]-1-piperazinyl]benzamide. Refer to Chart E A mixture of 6,8-dichloro-2-(chloromethyl)imidazo[1,2-a]pyridine (Example 19, Step 1; 0.301 g), 4-(piperazin-1-yl)benzamide (Example 3, Step 1; 0.2916 g), triethylamine (Aldrich; 0.21 mL), and ethylene glycol (2 mL) is stirred for 1 h at 80–85° C. The mixture is then allowed to cool and water is added. The solids are collected, washed with water and hexane, and dried under reduced pressure. The solid is then adsorbed onto silica gel and chromatographed using methanol/dichloromethane (8/92). The appropriate fractions are combined and concentrated and the residue is crystallized from dichloromethane/methanol to give 0.2938 g of the title compound; mp 234–235° C.; MS m/z 403,405; IR (mineral oil) 1606, 1668, 1392, 1522, 1241 cm$^{-1}$; $^1$H NMR (CDCl$_3$) δ2.74, 3.35, 3.83, 6.89, 7.27, 7.63, 7.72, 8.10.

EXAMPLE 23

6-Bromo-2-[[4-(4-chlorophenyl)-1-piperazinyl]methyl]-imidazo[1,2-a]pyridine. Refer to Chart E A mixture of 6-bromo-2-(chloromethyl)imidazo[1,2-α]pyridine (Example 15, Step 1; 0.3042 g), 1-(4-chlorophenyl)piperazine dihydrochloride (Aldrich; 0.3708 g), triethylamine (Aldrich; 0.55 mL), and ethylene glycol (5.6 mL) is stirred for 1 h at 80° C. After cooling, the mixture is partitioned between water and dichloromethane. The combined organic layers are washed with brine, dried with MgSO$_4$, and concentrated under reduced pressure. The residue is chromatographed on silica gel using methanol/dichloromethane (4/96) to give, after crystallization from ethyl acetate/methanol/dichlormetane, 0.1756 g of the title compound; mp 154–155° C.; MS m/z 404, 406, 408; IR (mineral oil) 1495, 1500, 1224, 823, 812 cm$^{-1}$; $^1$H NMR (CDCl$_3$) δ2.72, 3.19, 3.76, 6.83, 7.20, 7.22, 7.47, 7.52, 8.24.

EXAMPLE 24

8-Chloro-2-[[4-(4-fluorophenyl)-1-piperazinyl]methyl]-6-trifluoromethylimidazo[1,2-a]pyridine. Refer to Chart E Step 1. 8-Chloro-2-(chloromethyl)-6-trifluoromethylimidazo[1,2-α]pyridine A mixture of 2-amino-3-chloro-5-trifluoromethyl)pyridine (Aldrich; 5.1274 g), 1,3-dichloroacetone (Aldrich; 3.9523 g), and dimethoxyethane (23.5 mL) is stirred overnight at room temperature. The mixture is then stirred at 50–55° C. for 4.5 h and again overnight at room temperature, at which time the mixture is concentrated under reduced pressure. Ethanol is added and the mixture is stirred at reflux for 4 h. After stirring overnight at room temperature, the mixture is again stirred at reflux for several hours. After cooling, the solvent is removed under reduced pressure. The residue is partitioned between saturated sodium bicarbonate and dichloromethane. The combined organic layers are dried with MgSO$_4$, concentrated under reduced pressure, and the residue is chromatographed on silica gel using methanol/dichloromethane (1/99). The appropriate fractions are combined and concentrated and the residue is crystallized from ethyl acetate/hexane to give 1.86 g of 8-chloro-2-(chloromethyl)-6-trifluoromethylimidazo[1,2-α]pyridine; mp 75–77° C.; MS m/z 268, 270; IR (mineral oil) 1136, 1316, 1168, 869, 738 cm$^{-1}$; $^1$H NMR (CDCl$_3$) δ4.81. 7.45, 7.82, 8.43.

Step 2. 8-Chloro-2-[[4-(4-fluorophenyl)-1-piperazinyl]methyl]-6-trifluoromethylimidazo[1,2-a]pyridine A mixture of 8-chloro-2-(chloromethyl)-6-trifluoromethylimidazo[1,2-α]pyridine (0.341 g), 1-(4-fluorophenyl)piperazine (Aldrich; 0.264 g), triethylamine (Aldrich; 0.21 mL), and ethylene glycol (2 mL) is stirred for 2.25 h at 80–85° C. After cooling, the mixture is partitioned between water and dichloromethane and the combined inorganic layers are washed with brine, dried with MgSO$_4$, and concentrated under reduced pressure. The residue is chromatographed on silica gel using methanol/dichloromethane (2/98) and the appropriate fractions combined, concentrated, and crystallized from ether/hexane to give 0.339 g of the title compound; mp 91–97° C.; MS m/z 412, 414; IR (mineral oil) 1322, 1161, 1153, 1512, 1171 cm$^{-1}$; $^1$H NMR (CDCl$_3$) δ2.76, 3.15, 3.87, 6.88, 6.96, 7.41, 7.75, 8.41.

EXAMPLE 25

6-Chloro-2-[[4-(2-fluorophenyl)-1-piperazinyl]methyl]-imidazo[1,2-a]pyridine. Refer to Chart E Following the general procedure of Example 11 and making non-critical variations, 6-chloro-2-(chloromethyl)imidazo[1,2-α]pyridine (Example 4, Step 1; 0.294 g) and 1-(2-fluorophenyl)piperazine hydrochloride (Aldrich; 0.366 g) are converted to 0.268 g of the title compound after chromatography on silica gel using methanol/dichloromethane (6/94) and crystallization from ethyl acetate/hexane; mp 107–108° C.; MS m/z 344, 346; IR (mineral oil) 1501, 1221, 752, 1335, 927 cm$^{-1}$; $^1$H NMR (CDCl$_3$) δ2.76, 3.13, 3.78, 6.95, 7.03, 7.12, 7.52, 8.14.

EXAMPLE 26

6-Chloro-2-[(4-phenyl-1-piperazinyl)methyl]imidazo[1,2-a]pyridine. Refer to Chart E Following the general procedure of Example 11 and making non-critical variations, 6-chloro-2-(chloromethyl)

imidazo[1,2-α]pyridine (Example 4, Step 1; 0.296 g) and 1-phenylpiperazine hydrochloride (Aldrich; 0.333 g) are converted to 0.279 g of the title compound after chromatography on silica gel and crystallization from dichloromethane/ethyl ether/hexane; mp 128.5–130.5° C.; MS m/z 326, 328; IR (mineral oil) 1217, 1073, 1501, 921, 1600 cm$^{-1}$; $^1$H NMR (CDCl$_3$) δ2.74, 3.24, 3.77, 6.85, 6.92, 7.12, 7.26. 7.52. 8.13.

EXAMPLE 27

4-[4-[(8-Chloro-6-trifluoromethylimidazo[1,2-a] pyridin-2-yl)methyl]-1-piperazinyl]benzamide. Refer to Chart E Following the general procedure of Ex. 22 and making non-critical variations. 8-chloro-2-(chloromethyl)-6-trifluoromethylimidazo[1,2-α]pyridine (Example 24, Step 1; 0.347 g), 4-(piperazin-1-yl)benzamide (Example 3, Step 1; 0.293 g), triethylamine (0.21 mL) and ethylene glycol (2 mL) give 0.216 g of the title compound after crystallization from methanol/ethyl acetate; mp 205–206° C.; m/s m/z 437, 439; IR (mineral oil) 1142, 1644, 1616, 1610, 1321 cm$^{-1}$; $^1$H NMR (CDCl$_3$) δ2.74, 3.35, 3.86, 6.89, 7.42, 7.72, 7.75, 8.42.

EXAMPLE 28

6-Chloro-2-[[4-(3,4-dichlorophenyl)-1-piperazinyl]-methyl]imidazo[1,2-a]pyridine. Refer to Chart E Following the general procedure of Example 11 and making non-critical variations, 6-chloro-2-(chloromethyl) imidazo[1,2-α]pyridine (Example 4, Step 1; 0.493 g) and 1-(3,4-dichlorophenyl)piperazine (Aldrich; 0.636 g) are converted to 0.404 g of the title compound after chromatography on silica gel and crystallization from ethyl ether/hexane; mp 122.5–123.5° C.; MS m/z 394; IR (mineral oil) 1339, 1488, 804, 1072, 2807 cm$^{-1}$; $^1$H NMR (CDCl$_3$) δ2.72, 3.21, 3.77, 6.72, 6.94, 7.13, 7.26, 7.52, 8.14.

EXAMPLE 29

3-Chloro-4-[4-[(6-chloroimidazo[1,2-a]pyridin-2-yl) methyl]-1-piperazinyl]benzonitrile. Refer to Chart E
Step 1. 3-Chloro-4-(piperazin-1-yl)benzonitrile. Refer to Chart C A mixture of 3,4-dichlorobenzonitrile (Lancaster; 3.003 g), piperazine (Aldrich; 7.485 g), and DMF (10 mL) is stirred for 2.5 h at 100° C. After cooling, DMF is removed under reduced pressure and the residue is partitioned between dichloromethane and saturated aq. sodium bicarbonate. The organic layers are dried with MgSO$_4$ and concentrated under reduced pressure. The residue is chromatographed on silica gel using methanol/dichloromethane (8/92) to give 1.3785 g of 3-chloro-4-(piperaziny-1-yl) benzonitrile; mp 85–87° C.; MS m/z 221, 223; IR (mineral oil) 2225, 3338, 1451, 826, 1236, 1594 cm$^{-1}$; $^1$H NMR (CDCl$_3$) δ3.09, 7.03, 7.51, 7.62.
Step 2. 3-Chloro-4-[4-[(6-chloroimidazo[1,2-a]pyridin-2-yl) methyl]-1-piperazinyl]benzonitrile A mixture of 6-chloro-2-(chloromethyl)imidazo[1,2-a] pyridine (Example 4, Step 1; 0.140 g), 3-chloro-4-(piperazin-1-yl)benzonitrile (0.155 g), triethylamine (0.078 g), and THF (2.5 mL) is heated at reflux for 5.5 h and then stirred overnight at room temperature. A few drops of triethylamine are then added and the mixture is stirred an additional 4 h at reflux. After cooling, the mixture is concentrated and the residue is partitioned between dichloromethane and aq. sodium bicarbonate. The organic layers are dried over sodium sulfate and concentrated. Chromatography of the residue on silica gel using methanol/dichloromethane (4/96) gives 0.238 g of the title compound. A portion of the material is recrystallized from ethyl acetate/ethyl ether/hexane; mp 137–138° C.; MS m/z 385, 387; IR (mineral oil) 1501, 2225, 1130, 1342, 1490 cm$^{-1}$. $^1$H NMR (CDCl$_3$) δ2.77, 3.21, 3.79, 7.03, 7.14, 7.47–7.54, 7.61, 8.14.

EXAMPLE 30

3-Chloro-4-[4-[(6-chloroimidazo[1,2-a]pyridin-2-yl) methyl]-1-piperazinyl]benzamide. Refer to Chart F A mixture of 3-chloro-4-[4-[(6-chloroimidazo[1,2-a] pyridin-2-yl)methyl]-1-piperazinyl]benzonitrile (Example 29; 0.122 g), NaOH (0.063 g), 30% hydrogen peroxide (2 drops), and tert-butanol (2 mL) is stirred at 80° C. for 4 h, after which it is cooled and concentrated under reduced pressure. The residue is partitioned between dichloromethane and aq. sodium bicarbonate. The organic layers are dried over sodium sulfate and concentrated. The solids remaining suspended in the aqueous layer are collected, washed with water, dried under reduced pressure, and combined with the solids obtained from concentration of the organic layers. The solids are taken up in dichloromethane and methanol with warming and filtered through a cotton plug to remove insolubles. The filtrate is then concentrated and the residue is crystallized from dichloromethane/hexane to give 0.0745 g of the title compound; mp 254–256° C.; MS m/z 403, 405; IR (mineral oil) 1413, 1235, 1597, 800, 1328 cm$^{-1}$. $^1$H NMR (DMSOd$_6$) δ2.64, 3.05, 3.69, 7.17, 7.25, 7.37, 7.55, 7.79, 7.84, 7.89, 7.96, 8.80.

EXAMPLE 31

6-Chloro-2-[[4-(2,4-dichlorophenyl)-1-piperazinyl]-methyl]imidazo[1,2-a]pyridine. Refer to Chart E
Step 1. 1-(2,4-Dichlorophenyl)piperazine A mixture of 1,3-dichloro-4-fluorobenzene (Aldrich; 4.21 g), piperazine (Aldrich; 11.0 g), and N,N-dimethylacetamide (Aldrich; 15 mL) is heated at 165° C. for 6.5 h. After cooling, the mixture is partitioned between dichloromethane and aq. sodium bicarbonate. The organic layers are dried over sodium sulfate and concentrated under reduced pressure to give 4.48 g of 1-(2,4-dichlorophenyl) piperazine. $^1$H NMR (CDCl$_3$) δ3.00, 3.06, 6.96, 7.19, 7.36.
Step 2. 6-Chloro-2-[[4-(2,4-dichlorophenyl)-1-piperazinyl] methyl]imidazo[1,2-a]pyridine A mixture of 6-chloro-2-(chloromethyl)imidazo[1,2-a] pyridine (Example 4. Step 1; 0.374 g), 1-(2,4-dichlorophenyl)piperazine (0.430 g), triethylamine (0.19 g), and ethylene glycol (2 mL) is stirred for 2 h at 80° C. after which an additional 0.0374 g of 6-chloro-2-(chloromethyl) imidazo[1,2-a]pyridine is added. After stirring for another 60 min, the mixture is cooled and partitioned between dichloromethane and aq. sodium bicarbonate. The organic layers are dried over sodium sulfate. concentrated, and chromatographed on silica gel using methanol/dichloromethane (4/96) to give 0.606 g of material. Crystallization from dichloromethane/hexane gives 0.518 g of the title compound; mp 136.5–137.5° C.; MS m/z 394, 396; IR (mineral oil) 1479, 1342, 2808, 1454, 1072 cm$^{-1}$. $^1$H NMR (CDCl$_3$) δ2.78. 3.09, 3.80, 6.96, 7.11–7.20, 7.35, 7.52, 7.55, 8.14.

The maleic acid salt is prepared by dissolving 6-chloro-2-[[4-(2,4-dichlorophenyl)-1-piperazinyl]methyl]imidazo [1,2-a]pyridine (0.161 g) in methanol/dichloromethane and adding a solution of maleic acid (0.0472 g) in methanol.

After five min, the mixture is concentrated under reduced pressure. Ethyl acetate is added to the residue, followed by hexane and dichloromethane. The resulting crystals are collected and dried to give 0.192 g of the maleic acid salt of 6-chloro-2-[[4-(2,4-dichlorophenyl)-1-piperazinyl]methyl] imidazo[1,2-a]pyridine; mp 149–150° C.

In a similar manner, the methanesulfonic acid salt is prepared from 6-chloro-2-[[4-(2,4-dichlorophenyl)-1-piperazinyl/methyl]imidazo[1,2-a]pyridine (0.1006 g) and methanesulfonic acid (0.0244 g), with crystallization from ethyl acetate, to give 0.115 g of 6-chloro-2-[[4-(2,4-dichlorophenyl)-1-piperazinyl]methyl]imidazo[1,2-a]pyridine methanesulfonate as a hygroscopic material.

In a similar manner, the sulfate salt is prepared from 6-chloro-2-[[4-(2,4-dichlorophenyl)-1-piperazinyl]methyl]imidazo[1,2-a]pyridine (0.126 g) and concentrated sulfuric acid (0.0312 g), with crystallization from methanol/dichloromethane/hexane to give 0.129 g of the sulfate salt of 6-chloro-2-[[4-(2,4-dichlorophenyl)-1-piperazinyl]methyl]imidazo[1,2-a]pyridine; mp: sharp transition at 170.5° C. and then further gradual melting to about 210° C.

The dihydrochloride salt is prepared from 6-chloro-2-[[4-(2,4-dichlorophenyl)-1-piperazinyl]methyl]imidazo[1,2-a]pyridine (0.055 g) and a solution of hydrogen chloride in methanol. After allowing the mixture to stand for several minutes, the solvent is removed under reduced pressure and the residue is crystallized from ethyl acetate to give 0.053 g of 6-chloro-2-[[4-(2,4-dichlorophenyl)-1-piperazinyl] methyl]imidazo[1,2-a]pyridine dihydrochloride; mp 243–253° C.

The fumaric acid salt is prepared by adding fumaric acid (0.0399 g) to a solution of 6-chloro-2-[[4-(2,4-dichlorophenyl)-1-piperazinyl]methyl]imidazo[1,2-a]pyridine (0.136 g) in dichloromethane. Methanol is added to the mixture and after several minutes the solvents are removed under reduced pressure. Ethyl acetate is added to the residue and upon warming, crystals form to give 0.128 g of the fumaric acid salt of 6-chloro-2-[[4-(2,4-dichlorophenyl)-1-piperazinyl]methyl]imidazo[1,2-a]pyridine after collection and drying; mp 117–119° C. (shrinkage).

In a similar manner, the sulfuric acid salt is prepared from 6-chloro-2-[[4-(2,4-dichlorophenyl)-1-piperazinyl]methyl]imidazo[1,2-a]pyridine (0.125 g) and sulfuric acid (0.0307 g), with crystallization from methanol/ethyl acetate, to give 0.145 g of 6-chloro-2-[[4-(2,4-dichlorophenyl)-1-piperazinyl]methyl]imidazo[1,2-a]sulfuric acid salt; mp 134–137° C.

EXAMPLE 32

5-Chloro-2-[4-[(6-chloroimidazo[1,2-a]pyridin-2-yl) methyl]-1-piperazinyl]benzonitrile. Refer to Chart E Step 1. 5-Chloro-2-(piperazin-1-yl)benzonitrile. Refer to Chart C A mixture of 2,5-dichlorobenzonitrile (Lancaster; 2.994 g), piperazine (Aldrich; 7.616 g), and DMF (10 mL) is stirred for 4.5 h at 100° C. After cooling, the DMF is removed under reduced pressure and the residue is partitioned between dichloromethane and saturated aq. sodium bicarbonate. The organic layers are dried with MgSO$_4$ and concentrated under reduced pressure. The residue is chromatographed on silica gel using methanol/dichloromethane (8/92) and the appropriate fractions are combined and concentrated to give 0.79 g of 5-chloro-2-(piperazin-1-yl) benzonitrile; MS m/z 221; IR (mineral oil) 1489, 802, 829, 2223, 845 cm$^{-1}$; $^1$H NMR (CDCl$_3$) δ3.09, 3.18, 6.94, 7.43, 7.52.

Step 2. 5-Chloro-2-[4-[(6-chloroimidazo[1,2-a]pyridin-2-yl) methyl]-1-piperazinyl]benzonitrile Following the general procedure of Example 11 and making non-critical variations, 6-chloro-2-(chloromethyl) imidazo[1,2-α]pyridine (Example 4, Step 1; 0.292 g) and 5-chloro-2-(piperazin-1-yl)benzonitrile (0.385 g) are converted to 0.349 g of the title compound after chromatography on silica gel and crystallization from ethyl ether/dichloromethane/hexane. mp 191–191.5° C.; MS m/z 385, 387; IR (mineral oil) 1486, 1330, 806, 1495, 826 cm$^{-1}$; $^1$H NMR (CDCl$_3$) δ2.77, 3.24, 3.78, 6.93, 7.12, 7.42, 7.51, 8.14.

EXAMPLE 33

6-Chloro-2-[[4-[5-(trifluoromethyl)pyridin-2-yl]-1-piperazinyl]methyl]imidazo[1,2-a]pyridine. Refer to Chart E Step 1. 1-(5-Trifluoromethylpyridin-2-yl)piperazine. Refer to Chart C A mixture of 2-chloro-5-trifluoromethylpyridine (Aldrich; 2.296 g), piperazine (5.45 g), and water is heated at 100° C. for 16 h. After cooling, the mixture is partitioned between dichloromethane and aq. sodium bicarbonate. The organic layers are dried over sodium sulfate and concentrated. The residue is chromatographed on silica gel using methanol/dichloromethane (8/92) with about 0.5% ammonium hydroxide present, to give 2.20 g of 1-(5-trifluoromethylpyridin-2-yl)piperazine; mp 45–47° C.; IR (mineral oil) 1127, 1323, 1319, 1118, 1614 cm$^{-1}$; $^1$H NMR (CDCl$_3$) δ2.98, 3.62, 6.63, 7.62, 8.40.

Step 2. 6-Chloro-2-[[4-[5-(trifluoromethyl)pyridin-2-yl]-1-piperazinyl]methyl]imidazo[1,2-a]pyridine A mixture of 1-(5-trifluoromethylpyridin-2-yl)piperazine (0.4803 g), 6-chloro-2-(chloromethyl) imidazo[1,2-a] pyridine (Example 4, Step 1; 0.4177 g), triethylamine (0.231 g), and ethylene glycol (1 mL) is stirred at 80° C. for 70 min. after which additional 6-chloro-2-(chloromethyl)imidazo[1,2-a]pyridine (0.072 g) is added; thirty minutes later another portion (0.0517 g) is added. After stirring for a total of 2 h, the mixture is cooled and partitioned between dichloromethane and aq. sodium bicarbonate. The organic layers are dried over sodium sulfate and concentrated. Chromatography on silica gel using methanol/dichloromethane (4/96) and crystallization from ethyl ether/hexane gives 0.549 g of the title compound; mp 81–82° C.; MS m/z 395; IR (mineral oil) 1617, 1332, 1328, 1112, 1082 cm$^{-1}$. $^1$H NMR (CDCl$_3$) δ2.68, 3.69, 3.77, 6.62, 7.14, 7.52, 7.55, 7.61, 8.14, 8.38.

EXAMPLE 34

5-Chloro-2-[4-[(6-methylimidazo[1,2-a]pyridin-2-yl) methyl]-1-piperazinyl]benzonitrile. Refer to Chart E Following the general procedure of Example 9, Step 2, and making non-critical variations, 2-(chloromethyl)-6-methylimidazo[1,2-α]pyridine (Example 9, Step 1; 0.2792 g) and 5-chloro-2-(piperazin-1-yl)benzonitrile (Example 32, Step 1; 0.4029 g) give 0.176 g of the title compound after chromatography and crystallization from ethyl ether/dichloromethane; mp 135–136° C.; MS m/z 365, 367; IR (mineral oil) 1486, 803, 1341, 825, 1333 cm$^{-1}$; $^1$H NMR (CDCl$_3$) δ2.31, 2.78, 3.25, 3.77, 6.92, 7.00, 7.39–7.50, 7.86.

EXAMPLE 35

6-Chloro-2-[[4-(5-chloropyridin-2-yl)-1-piperazinyl]-methyl]imidazo[1,2-a]pyridine. Refer to Chart E Step 1. 1-(5-Chloropyridin-2-yl)piperazine. Refer to Chart C Following the general procedure of Example 33, Step 1, and making non-critical variations, 2,5-dichloropyridine (Aldrich; 5.10 g), piperazine (14.8 g), water (50 mL), and N,N-dimethylacetamide (2 mL) give 3.42 g of 1-(5-chloropyridin-2-yl)piperazine; mp 92–107° C.; IR 1480, 1244, 1390, 1589 815 cm$^{-1}$; $^1$H NMR (CDCl$_3$) δ2.98, 3.47, 6.58, 7.42, 8.11.

Step 2. 6-Chloro-2-[[4-(5-chloropyridin-2-yl)-1-piperazinyl]methyl]imidazo[1,2-a]pyridine Following the general procedure of Example 33, Step 2, and making non-critical variations, 1-(5-chloropyridin-2-yl)piperazine (0.424 g), 6-chloro-2-(chloromethyl)imidazo[1,2-a]pyridine (Example 4, Step 1; 0.517 g), triethylamine (0.282 g), and ethylene glycol (2 mL) give, after crystallization from dichloromethane/ethyl ether, 0.621 g of the title compound; mp 137–138° C.; MS m/z 361, 363; IR 1593, 1480, 1245, 1324, 801, 1304 cm$^{-1}$; $^1$H NMR (CDCl$_3$) δ2.67, 3.55, 3.75, 6.57, 7.13, 7.41, 7.52, 7.53, 8.10, 8.14.

EXAMPLE 36

6-Chloro-2-[[4-(3-methoxyphenyl)-1-piperazinyl]methyl]-imidazo[1,2-a]pyridine. Refer to Chart E Following the general procedure of Example 11 and making noncritical variations, 6-chloro-2-(chloromethyl) imidazo[1,2-a]pyridine (Example 4, Step 1; 0.409 g), 1-(3-methoxyphenyl)piperazine dihydrochloride (Aldrich; 0.450 g), triethylamine (Aldrich; 0.686 g), and ethylene glycol (2 mL) give 0.440 g of the title compound after chromatography (silica gel, methanol/dichloromethane, 4/96) and crystallization from dichloromethane/ethyl ether/hexane; mp 132–133.5° C.; MS m/z 356; IR (mineral oil) 805, 2817, 1198, 1171, 1580, 1502 cm$^{-1}$. $^1$H NMR (CDCl$_3$) δ2.74, 3.24, 3.78, 6.41, 6.46, 6.55, 7.11–7.19, 7.52, 7.56, 8.14.

EXAMPLE 37

2-[[4-(2,4-Dichlorophenyl)-1-piperazinyl]methyl]-6-ethoxyimidazo[1,2-a]pyridine. Refer to Chart E Step 1. 2-(Chloromethyl)-6-ethoxyimidazo[1,2-α]pyridine. Refer to Chart A A mixture of 2-amino-5-ethoxypyridine (1.53 g; prepared by the method of Lombardino, *J. Med. Chem.* 1981, 24, 39–42), 1,3-dichloroacetone (Aldrich; 1.115 g), and dimethoxyethane (7 mL) is stirred overnight at room temperature. The mixture is concentrated under reduced pressure and ethanol (22.5 mL) is added. After the mixture is stirred for 30 min at 80° C., it is cooled and then concentrated under reduced pressure. The residue is partitioned between dichloromethane and saturated aq. sodium bicarbonate. The combined organic layers are dried with MgSO$_4$ and concentrated under reduced pressure. The residue is chromatographed on silica gel using methanol/dichloromethane (4/96) and crystallized from ether/dichlormethane/hexane to give 0.94 g of 2-(chloromethyl)-6-ethoxyimidazo[1,2-α]pyridine in three crops; mp 95–96° C.; MS m/z 210, 212; IR (mineral oil) 1192, 1263, 810, 1537, 1511 cm$^{-1}$; $^1$H NMR (CDCl$_3$) δ1.45, 3.97, 4.75, 6.98, 7.46, 7.55, 7.58.

Step 2. 2-[[4-(2,4-Dichlorophenyl)-1-piperazinyl]methyl]-6-ethoxyimidazo[1,2-a]pyridine A mixture of 2-(chloromethyl)-6-ethoxyimidazo[1,2-α] pyridine (0.204 g), 1-(2,4-dichlorophenyl) piperazine (Example 31, Step 1; 0.2283 g), triethylamine (Aldrich; 0.15 mL), and THF (1.3 mL) is stirred at 75° C. until the reaction is judged complete by thin layer chromatography. The cooled mixture is concentrated under reduced pressure and partitioned between dichloromethane and saturated aq. sodium bicarbonate. The combined organic layers are dried with MgSO$_4$ and concentrated under reduced pressure. The residue is chromatographed on silica gel using methanol/ dichloromethane (2/98) and crystallized from ethyl acetate/ ether to give 0.0936 g of the title compound; mp 171–172° C.; MS m/z 404, 406; IR (mineral oil) 1478, 1189, 797, 1508, 1273 cm$^{-1}$; $^1$H NMR (CDCl$_3$) δ1.45, 2.77, 3.08, 3.77, 3.98, 6.94, 7.17, 7.34, 7.45, 7.47, 7.60.

EXAMPLE 38

4-[4-[(6-Chloroimidazo[1,2-a]pyridin-2-yl)methyl]-1-piperazinyl]-3-fluorobenzonitrile. Refer to Chart E Step 1. 3-Fluoro-4-(piperazin-1-yl)benzonitrile. Refer to Chart C A mixture of 3,4-difluorobenzonitrile (Aldrich; 4.076 g), piperazine (Aldrich; 12.554 g), and N,N-dimethylacetamide (20 mL) is stirred for 1.3 h at 120° C. The mixture is then concentrated under reduced pressure to remove some of the N,N-dimethylacetamide and then partitioned between dichloromethane and saturated aq. sodium bicarbonate. The combined organic layers are dried with MgSO$_4$ and concentrated under reduced pressure. The residue is crystallized from dichloromethane/ethyl acetate/methanol to give 1.99 g of material in two crops. The combined solids are then chromatographed on silica gel using methanol/ dichloromethane (8/92) and the appropriate fractions combined and concentrated. The residue is slurried in ethyl acetate, followed by the addition of methanol/ dichloromethane and warming. The mixture is concentrated and the first solids to precipitate are removed by filtration. The filtrate is further concentrated to give 3.33 g of 3-fluoro-4-(piperazin-1-yl)benzonitrile; mp 85–85.5° C. ; IR (mineral oil) 1250, 897, 1613, 1505, 1515 cm$^{-1}$; $^1$H NMR (CDCl$_3$) δ1.90, 3.05, 3.18, 6.92, 7.26, 7.36.

Step 2. 4-[4-[(6-Chloroimidazo[1,2-a]pyridin-2-yl)methyl]-1-piperazinyl]-3-fluorobenzonitrile A mixture of 6-chloro-2-(chloromethyl)imidazo[1,2-α] pyridine (Example 4, step 1, 0.857 g), 3-fluoro-4-(piperazin-1-yl)benzonitrile (1.039 g), triethylamine (0.75 mL), and THF (6 mL) is stirred for 3 h at 75–80° C. The mixture is then concentrated under reduced pressure and the residue is partitioned between dichloromethane and saturated sodium bicarbonate. The combined organic layers are dried with MgSO$_4$ and concentrated under reduced pressure. The residue is chromatographed on silica gel using methanol/ dichloromethane (4/96). The appropriate fractions are combined and concentrated. Ethyl ether is added to the residue and the resulting solid is collected, washed with additional ethyl ether, and dried under reduced pressure to give 1.25 g of the title compound. A portion of this material is recrystallized from ethyl acetate; mp 132–133° C. ; IR (mineral oil) 1255, 1513, 1246, 801, 1504 cm$^{-1}$; $^1$H NMR (CDCl$_3$) δ2.74, 3.26, 3.77, 6.90, 7.13, 7.25, 7.34, 7.53, 8.13.

EXAMPLE 39

2-[[4-(2,4-Dichlorophenyl)-1-piperazinyl]methyl]-6-methoxyimidazo[1,2-a]pyridine. Refer to Chart E Step 1. 2-(Chloromethyl)-6-methoxyimidazo[1,2-α] pyridine. Refer to Chart A A mixture of 2-amino-5-methoxypyridine (0.5036 g; prepared by the method of Lombardino, *J. Med. Chem.* 1981, 24, 39–42), 1,3-dichloroacetone (Aldrich; 0.3935 g), and dimethoxyethane (2.5 mL) is stirred overnight at room temperature. The mixture is concentrated under reduced pressure and ethanol (7.9 mL) is added. After the mixture has stirred for 30 min at 80° C., it is cooled and concentrated under reduced pressure. The residue is partitioned between dichloromethane and saturated aq. sodium bicarbonate and the combined organic layers are dried with $MgSO_4$ and concentrated under reduced pressure. The residue is chromatographed on silica gel using methanol/dichloromethane (4/96) to give 0.1392 g of 2-(chloromethyl)-6-methoxyimidazo[1,2-α]pyridine; $^1$H NMR (CDCl$_3$) δ3.82, 4.75, 6.99, 7.48, 7.56, 7.59.

Step 2. 2-[[4-(2,4-Dichlorophenyl)-1-piperazinyl]methyl]-6-methoxyimidazo[1,2-a]pyridine A mixture of 2-(chloromethyl)-6-methoxyimidazo[1,2-a]pyridine (0.1392 g), 1-(2,4-dichlorophenyl)piperazine (Example 31, Step 1; 0.1662 g), triethylamine (Aldrich; 0.11 mL), and THF (2 mL) is stirred at 75° C. until the reaction is complete by thin layer chromatography. The cooled mixture is concentrated under reduced pressure and partitioned between dichloromethane and saturated aq. sodium bicarbonate. The combined organic layers are dried with $MgSO_4$ and concentrated under reduced pressure. The residue is chromatographed on silica gel using methanol/dichloromethane (4/96) and crystallized from ethyl acetate/ether to give 0.132 g of the title compound in two crops; mp 129.5–130.5° C.; MS m/z 390, 392; IR (mineral oil) 1479, 1166, 799, 1510, 1219 cm$^{-1}$; $^1$H NMR (CDCl$_3$) δ2.76, 3.08, 3.77, 3.81, 6.93, 6.97, 7.17, 7.34, 7.45, 7.49, 7.60.

EXAMPLE 40

2-[4-[(6-Chloroimidazo[1,2-a]pyridin-2-yl)methyl]-1-piperazinyl]-4-fluorobenzonitrile. Refer to Chart E Step 1. 1-(2-Cyano-5-fluorophenyl)piperazine. Refer to Chart C A mixture of piperazine (Aldrich; 3.99 g), 2,4-difluorobenzonitrile, and N,N-dimethylacetamide (20 mL) is stirred for 1.5 h at 122° C. After cooling, the mixture is partitioned between dichloromethane and satd. aq. sodium bicarbonate. The organic layers are dried over magnesium sulfate and concentrated. The residue is chromatographed on silica gel and the appropriate fractions are combined and concentrated to give 1.44 g of 1-(2-cyano-5-fluorophenyl)piperazine; $^1$H NMR (CDCl$_3$) δ3.01, 3.30, 6.56, 6.63, 7.40.

Step 2. 2-[4-[(6-Chloroimidazo[1,2-a]pyridin-2-yl)methyl]-1-piperazinyl]-4-fluorobenzonitrile Following the general procedure of Example 39, Step 2, and making non-critical variations, 6-chloro-2-(chloromethyl)imidazo[1,2-α]pyridine (Example 4, Step 1; 0.298 g), 1-(2-cyano-5-fluorophenyl)piperazine (0.309 g), and THF (2 mL) are converted to product, which is then chromatographed on silica gel using methanol/dichlormethane (2/98 to 4/96). Crystallization from dichloromethane/hexane, gives 0.348 g of material, which is recrystallized from ethyl acetate/dichloromethane to give 0.201 g of the title compound; mp 149–150° C.; MS m/z 369, 371; IR (mineral oil) 1625, 1260, 2221, 1514, 1332 cm$^{-1}$; $^1$H NMR (CDCl$_3$) δ2.69, 3.37, 3.76, 3.53, 6.61, 7.13, 7.39, 7.52, 7.53, 8.14.

EXAMPLE 41

6-Chloro-2-[[4-[3-(trifluoromethyl)phenyl]-1-piperazinyl]methyl]imidazo[1,2-a]pyridine. Refer to Chart E Following the general procedure of Example 39, Step 2, and making non-critical variations, 6-chloro-2-(chloromethyl)imidazo[1,2-α]pyridine (Example 4, Step 1; 0.2982 g) and 1-[3-(trifluoromethyl)phenyl]piperazine (Aldrich; 0.34 mL) are converted to product, followed by chromatography on silica gel using methanol/dichlormethane (2/98). Crystallization from ethyl acetate and then from ethyl acetate/dichloromethane gives 0.053 g of the title compound; mp 145–145.5° C.; MS m/z 394; IR (mineral oil) 1117, 1163, 1451, 1073, 1339 cm$^{-1}$; $^1$H NMR (CDCl$_3$) δ2.75, 3.28, 3.78, 7.12, 7.34, 7.52, 7.54, 8.14.

EXAMPLE 42

1-[4-[4-[(6-Chloroimidazo[1,2-a]pyridin-2-yl)methyl]-1-piperazinyl]phenyl]ethanone. Refer to Chart E Following the general procedure of Example 39, Step 2, 6-chloro-2-(chloromethyl) imidazo[1,2-α]pyridine (Example 4. Step 1; 0.294 g), 4-piperazinoacetophenone (Aldrich; 0.366 g), and THF (3 mL) are converted to product, which is chromatographed on silica gel using methanol/dichlormethane (2/98), followed by crystallization from ethyl acetate/dichloromethane, to give 0.270 g of the title compound in two crops; mp 185.5–187° C.; MS m/z 368; IR (mineral oil) 1600, 1661, 1252, 1327, 1197 cm$^{-1}$; $^1$H NMR (CDCl$_3$) δ2.52, 2.72, 3.40, 3.76, 6.86, 7.13, 7.52, 7.54, 7.86, 8.15.

EXAMPLE 43

6-Chloro-2-[(4-phenyl-1-piperidinyl)methyl]imidazo[1,2-a]pyridine. Refer to Chart E Following the general procedure of Example 39, Step 2 and making non-critical variations, 6-chloro-2-(chloromethyl)imidazo[1,2-α]pyridine (Example 4, Step 1; 0.307 g), 4-phenylpiperidine (Aldrich or Chart J; 0.2955 g), and THF (2 mL) are converted to product, which is chromatographed on silica gel using methanol/dichlormethane (4/96), followed by crystallization from ethyl acetate, to give 0.169 g of the title compound; mp 132–133° C.; MS m/z 325; IR (mineral oil) 1073, 801, 696, 1324, 1501 cm$^{-1}$; $^1$H NMR (CDCl$_3$) δ1.83, 2.20, 2.51, 3.14, 3.75, 7.11, 7.24, 7.52, 7.54, 8.13.

EXAMPLE 44

6-Chloro-2-[[4-(2,4-dichlorophenyl)-1-piperazinyl]methyl]-imidazo[1,2-a]pyridine-3-methanol. Refer to Chart G A mixture of 6-chloro-2-[[4-(2,4-dichlorophenyl)-1-piperazinyl]-methyl]imidazo[1,2-a]pyridine (Example 31, Step 2; 0.125 g), 37% formaldehyde in water (2 mL), and THF (2 mL) is stirred at 85° C. for 50 min, at which time an additional 1 mL of 37% formaldehyde in water is added. A third addition of 37% formaldehyde in water (1 mL) is made 1.5 h later. After the mixture has stirred for a total of 22 h, the heat is turned off and the mixture is allowed to stir at room temperature an additional 12 h. The mixture is then partitioned between dichloromethane and aq. sodium bicarbonate. Chromatography on silica gel using methanol/dichloromethane (3/97) gives 0.132 g of product, which after crystallization from dichloromethane/hexane gives 0.125 g of the title compound; mp 165–166° C.; MS m/z 424, 426; IR (mineral oil) 1479, 792, 1021, 816, 1502 cm$^{-1}$. $^1$H NMR (CDCl$_3$) δ2.79, 3.05, 3.90, 4.93, 6.1, 6.92, 7.17, 7.35, 7.52, 8.04.

EXAMPLE 45

6-Chloro-2-[[4-(2,4-dichlorophenyl)-1-piperazinyl]methyl]-3-[(phenylmethoxy)methyl]imidazo[1,2-a]pyridine monomethanesulfonate. Refer to Chart G To 6-chloro-2-[[4-(2,4-dichlorophenyl)-1-piperazinyl]methyl]imidazo[1,2-a]pyridine-3-methanol (Example 44;

0.0651 g) in THF (1 mL) is added sodium hydride (Aldrich, 60% dispersion in mineral oil; 0.0067 g). After 7 min, benzyl bromide (Aldrich; 0.020 mL) is added and the mixture is stirred for an additional 4.5 h. at which time it is partitioned between dichloromethane and aq. sodium bicarbonate/brine. The organic layers are filtered through sodium sulfate and concentrated, and the residue is chromatographed on silica gel using methanol/dichloromethane (2/98) to give 0.061 g of 6-chloro-2-[[4-(2,4-dichlorophenyl)-1-piperazinyl] methyl]-3-[(phenylmethoxy)methyl]imidazo[1,2-a] pyridine. The methanesulfonic acid salt is prepared by dissolving the product in dichloromethane and adding methanesulfonic acid (1 equivalent) and concentrating the mixture under reduced pressure. Crystallization from ethyl acetate/hexane affords 0.050 g of the title compound; mp 159–160.5° C.; MS m/z 514, 516; IR (mineral oil) 806, 1170, 1042, 1188, 1480 cm$^{-1}$. $^1$H NMR (CDCl$_3$) δ2.68, 3.02, 3.75, 4.57, 4.91, 6.92, 7.17, 7.36, 7.53, 8.14.

EXAMPLE 46

6-Bromo-2-[[4-(2,4-dichlorophenyl)-1-piperazinyl]
methyl]-imidazo[1,2-a]pyridine. Refer to Chart E A mixture of 6-bromo-2-(chloromethyl)imidazo[1,2-a] pyridine (Example 15, Step 1; 0.582 g), 1-(2,4-dichlorophenyl)piperazine (Example 31, Step 1; 0.548), triethylamine (Aldrich; 0.288 g), and THF (5 mL) is stirred at 80° C. for 6 h, at which time it is cooled and then partitioned between dichloromethane and aq. sodium bicarbonate. The organic layers are dried over sodium sulfate and concentrated. Chromatography of the residue on silica gel using methanol/dichloromethane (2/98) and crystallization gives 0.710 g of the title compound; mp 137–138° C.; MS m/z 438, 440; IR (mineral oil) 1479, 1341, 1058, 2810, 803 cm$^{-1}$. $^1$H NMR (CDCl$_3$) δ2.78, 3.09, 3.80, 6.96, 7.16–7.23, 7.35, 7.48, 7.55, 8.24.

EXAMPLE 47

6-Chloro-2-[[4-(3-chloro4-methoxyphenyl)-1-
piperazinyl]-methyl]imidazo[1,2-a]pyridine. Refer
to Chart E Step 1. 1-(3-Chloro-4-methoxyphenyl)piperazine. Refer to Chart B A mixture of 3-chloro-4-anisidine (Aldrich; 0.633 g), bis(2-chloroethyl)amine hydrochloride (Aldrich; 0.860 g), potassium carbonate (1.11 g), and N,N-dimethylacetamide (6 mL) is stirred at 100° C. for 17.5 h, at which time the mixture is cooled and partioned between dichloromethane and water/sodium bicarbonate. The organic layers are dried over sodium sulfate, concentrated, and the residue is chromatographed on silica gel using methanol/dichloromethane (8/92) to give 0.297 g of 1-(3-chloro-4-methoxyphenyl) piperazine. $^1$H NMR (CDCl$_3$) δ3.05, 3.86, 6.80, 6.87, 6.99.
Step 2. 6-Chloro-2-[[4-(3-chloro-4-methoxyphenyl)-1-piperazinyl]methyl]-imidazo[1,2-a]pyridine A mixture of 6-chloro-2-(chloromethyl)imidazo[1,2-a] pyridine (Example 4, Step 1; 0.290 g), 1-(3-chloro-4-methoxyphenyl)piperazine (0.271 g), triethylamine (Aldrich; 0.159 g), and ethylene glycol (2 mL) is stirred at 80° C. for 40 min, at which time another 0.031 g of 6-chloro-2-(chloromethyl)imidazo[1,2-a]pyridine is added; after another 45 min, an additional 0.025 g of 6-chloro-2-(chloromethyl)imidazo[1,2-a]pyridine is added. When the mixture has stirred for a total of 2 h, it is cooled and partitioned between dichloromethane and aq. sodium bicarbonate. The organic layers are dried over sodium sulfate and concentrated. The residue is chromatographed on silica gel using methanol/dichloromethane (2/98) to give 0.29 g of the title compound after crystallization from ethyl acetate/hexane; mp 99–100.5 ° C.; MS m/z 390, 392; IR (mineral oil) 1510, 1501, 795, 1072, 1321 cm$^{-1}$. $^1$H NMR (CDCl$_3$) δ2.75, 3.14, 3.78, 3.84, 6.83, 6.97, 7.13, 7.52, 7.55, 8.14.

EXAMPLE 48

6-Chloro-2-[[4-(2-pyrimidinyl)-1-piperazinyl]
methyl]imidazo[1,2-a]pyridine. Refer to Chart E A mixture of 6-chloro-2-(chloromethyl)imidazo[1,2-a] pyridine (Example 4, Step 1; 0.335 g), 1-(pyrimidin-2-yl) piperazine dihydrochloride (Aldrich; 0.395 g), triethylamine (Aldrich; 0.522 g), THF (5 mL), and dichloromethane (5 mL) is heated at 80° C. for 45 min and then at 60° C. for 5 h, at which time DMF (1 mL) is added. After stirring for a total of 10.5 h, the mixture is allowed to cool and stir at room temperature for an additional 12 h. The solvents are then removed under reduced pressure and the residue is partitioned between dichloromethane and aq. sodium bicarbonate. The organic layers are dried over sodium sulfate and concentrated. The residue is chromatographed on silica gel using methanol/dichloromethane (4/96) and the appropriate fractions are combined and concentrated to give 0.228 g of the title compound. Crystallization from methanol-dichloromethane-hexane gives 0.315 g of the title compound in two crops; mp 114–115° C.; MS m/z 328, 330; IR (mineral oil) 1481, 1357, 1584, 1439, 1253, 1548 cm$^{-1}$. $^1$H NMR (CDCl$_3$) δ2.64, 3.76, 3.87, 6.48, 7.12, 7.52, 7.54, 8.14, 8.30.

EXAMPLE 49

2-[[4-(2,4-Dichlorophenyl)-1-piperazinyl]methyl]-6-
(trifluoromethyl) imidazo[1,2-a]pyridine
monomethanesulfonate. Refer to Chart E Step 1. 2-(Chloromethyl)-6-(trifluoromethyl)imidazo[1,2-a] pyridine A mixture of 2-amino-5-trifluoromethylpyridine (Fluorochem; 3.19 g), 1,3-dichloroacetone (Aldrich; 3.00 g), and dimethoxyethane (Aldrich; 15 mL) is stirred at room temperature for 4 days. The resulting solid is collected and washed with several milliliters of dimethoxyethane. The solid is then taken up in ethanol (30 mL) and the mixture is heated at 80° C. for 2.5 h, at which time diisopropylethylamine (Aldrich: 3.5 mL) is added. After stirring with heating an additional 3.5 h, the mixture is cooled and the solvent is removed under reduced pressure. The residue is partitioned between dichloromethane and aq. sodium bicarbonate. The organic layers are filtered through sodium sulfate and concentrated; the residue is chromatographed on silica gel using methanol/dichloromethane (1/99) to give 3.33 g of 2-(chloromethyl)-6-(trifluoromethyl) imidazo[1,2-a]pyridine. $^1$H NMR (CDCl$_3$) δ4.78, 7.36, 7.69, 7.73, 8.48.
Step 2. 2-[[4-(2,4-Dichlorophenyl)-1-piperazinyl]methyl]-6-(trifluoromethyl) imidazo[1,2-a]pyridine monomethanesulfonate A mixture of 2-(chloromethyl)-6-(trifluoromethyl) imidazo[1,2-a]pyridine (0.452 g), 1-(2,4-dichlorophenyl) piperazine (Example 31, Step 1; 0.468 g), diisopropylethylamine (Aldrich; 0.299 g), and THF (4 mL) is stirred at reflux for 21 h. After cooling, the mixture is partitioned between dichloromethane and aq. sodium bicarbonate. The organic layers are dried over sodium sulfate, concentrated. and the residue chromatographed on silica gel using methanol/dichloromethane (2.5/97.5) to give 0.64 g of 2-[[4-

(2,4-dichlorophenyl)-1-piperazinyl]methyl]-6-(trifluoromethyl)imidazo[1,2-a]pyridine. The methanesulfonate salt is prepared by dissolving 2-[[4-(2,4-dichlorophenyl)-1-piperazinyl]methyl]-6-(trifluoromethyl) imidazo[1,2-a]pyridine in ethyl acetate/hexane and adding methanesulfonic acid (0.143 g) dissolved in methanol. The mixture is concentrated under reduced pressure and the residue is crystallized from ethyl acetate to give 0.691 g of the title compound; mp 161–162° C.; MS m/z 428; IR (mineral oil) 1162, 1225, 1033, 1130, 1142, 1337 cm$^{-1}$. $^1$H NMR (CDCl$_3$) δ2.78, 3.09, 3.83, 6.96, 7.18, 7.31, 7.35, 7.66, 7.68, 8.47.

EXAMPLE 50

2-[[4-(4-Chlorophenyl)-1-piperazinyl]methyl]-6-(trifluoromethyl) imidazo[1,2-a]pyridine. Refer to Chart E Following the same general procedure as for Example 49, Step 2, and making non-critical variations, 2-(chloromethyl)-6-trifluoromethylimidazo[1,2-a]pyridine. (Example 49, Step 1; 0.435 g), 1-(4-chlorophenyl)piperazine dihydrochloride (Aldrich; 0.550 g), diisopropylethylamine (Aldrich; 0.815 g), and THF (6 mL) give 0.30 g of 2-[[4-(4-chlorophenyl)-1-piperazinyl]methyl]-6-(trifluoromethyl) imidazo[1,2-a]pyridine after crystallization from ethyl acetate/hexane; mp 128–135° C.; MS m/z 394; IR (mineral oil) 1331, 1141, 1127, 1055, 1500, 830 cm$^{-1}$. $^1$H NMR (CDCl$_3$) δ2.74, 3.20, 3.80, 6.83, 7.19, 7.31, 7.66, 7.68, 8.47.

EXAMPLE 51

2-[[4-(4-Chlorophenyl)-1-piperazinyl]methyl]-6-phenylimidazo[1,2-a]pyridine. Refer to Chart H A mixture of 6-bromo-2-[[4-(4-chlorophenyl)-1-piperazinyl]methyl]imidazo[1,2-a]pyridine. (Example 23; 0.091 g), tetrakis(triphenylphosphine)palladium (0) (Aldrich; 0.0078 g), and dimethoxyethane (2 mL) is stirred at room temperature for 10 min, at which time phenylboric acid (Aldrich; 0.0306 g) is added, followed by sodium bicarbonate (0.0565 g) in water (1 mL). The mixture is stirred at reflux for 3 h and then allowed to cool. Dimethoxyethane is removed under reduced pressure and the residue is partitioned between dichloromethane and aq. sodium bicarbonate. The organic layers are dried over sodium sulfate and concentrated. The residue is chromatographed on silica gel using acetone/dichloromethane/methanol (50/200/1) to give 0.027 g of the title compound. MS m/z 402; $^1$H NMR (CDCl$_3$) δ2.76, 3.21, 3.80, 6.84, 7.19, 7.37–7.58, 7.61, 7.64, 8.26.

EXAMPLE 52

4-[4-[(6-Chloroimidazo[1,2-a]pyridin-2-yl)methyl]-1-piperazinyl]-3-fluorobenzamide. Refer to Chart F A mixture of 4-[4-[(6-chloroimidazo[1,2-a]pyridin-2-yl)methyl]-1-piperazinyl]-3-fluorobenzonitrile (Example 38; 0.298 g), pulverized NaOH (0.159 g), tert-butanol (3 mL), and 5 drops of 30% hydrogen peroxide in water is heated at 90° C. for 5.5 h. The mixture is then concentrated under reduced pressure and the resulting solids are slurried in water, collected by filtration, and washed and dried under reduced pressure. The solids are then crystallized from dichloromethane/methanol to give 0.180 g of material, which is chromatographed on silica gel using methanol/dichloromethane (4/96). After combining and concentrating the appropriate fractions, the residue is crystallized from ethyl acetate/dichloromethane/methanol to give 0.084 g of the title compound; mp 253–255° C.; MS m/z 387, 389; IR (mineral oil) 1435, 1620, 1678, 1225, 1505 cm$^{-1}$; $^1$H NMR (CDCl$_3$+CD$_3$OD) δ2.77, 3.38, 3.80, 6.94, 7.19, 7.53, 7.62, 8.23.

EXAMPLE 53

(RS)-4-[4-[(6-Chloroimidazo[1,2-a]pyridin-2-yl) methyl]-3-methylpiperazin-1-yl]benzamide. Refer to Chart E Step 1. (RS)-4-(3-Methylpiperazin-1-yl)benzamide. Refer to Chart C A mixture of 4-fluorobenzamide (Aldrich; 2.432 g), (RS)-2-methylpiperazine (Aldrich; 4.247 g), and water (9 mL) is heated at 100° C. for 7 days. The mixture is then cooled to 41° C. and water is added. The solid is collected, washed with water and toluene and dried under reduced pressure to give 3.37 g of (RS)-4-(3-methylpiperazin-1-yl)benzamide; $^1$H NMR (CDCl$_3$, CD$_3$OD) δ1.17, 2.48, 2.82, 2.94–3.15, 3.04, 3.68, 6.89, 7.73.

Step 2. (RS)-4-[4-[(6-Chloroimidazo[1,2-a]pyridin-2-yl) methyl]-3-methylpiperazin-1-yl]benzamide Following the general procedure of Example 39. Step 2, and making non-critical variations, 6-chloro-2-(chloromethyl)imidazo[1,2-α]pyridine (Example 4, Step 1; 0.201 g) and (RS)4-(2-methylpiperazine)benzamide (0.253 g) are converted to crude product, which is chromatographed on silica gel using methanol/dichlormethane (4/96 to 8/92), followed by crystallization from ethyl acetate/dichloromethane/methanol, to give 0.1454 g of material. Re-chromatography on silica gel using methanol/dichloromethane/NH$_4$OH (4/96/0.5) and trituration of the material from the product fractions with ethyl ether gives the title compound; mp 202–204° C.; MS m/z 383, 385; IR (mineral oil) 1609, 1393. 1251, 1681, 1423 cm$^{-1}$; $^1$H NMR (CDCl$_3$) δ1.20, 2.51, 2.86, 3.66, 3.96, 6.90, 7.03, 7.24, 7.55, 7.70, 7.72, 7.85, 8.79.

EXAMPLE 54

2-[[4-(4-Chlorophenyl)-1-piperazinyl]methyl]-8-methylimidazo[1,2-a]pyridine. Refer to Chart E Step 1. 2-(Chloromethyl)-8-methylimidazo[1,2-a]pyridine A mixture of 2-amino-3-picoline (Aldrich; 13.23 g), 1,3-dichloroacetone (Aldrich; 18.92 g), and dimethoxyethane (131 mL) is stirred at room temperature for 2 days. The mixture is then concentrated under reduced pressure and ethanol (100 mL) is added. The mixture is heated at 80° C. for 2.3 h. After cooling, the mixture is concentrated under reduced pressure and the residue is partitioned between saturated aq. sodium bicarbonate and dichloromethane. The combined organic layers are dried with MgSO$_4$ and concentrated under reduced pressure. The residue is chromatographed on silica gel first using methanol/dichloromethane (4/96) and a second time using methanol/dichloromethane (2/98). The appropriate fractions are combined and concentrated, and the residue is crystallized from ethyl acetate/dichloromethane/ether to give a first crop of 5.854 g and a second crop of 1.079 g of 2-(chloromethyl)-8-methylimidazo[1,2-a]pyridine; MS m/z 180, 182; IR (mineral oil) 752, 709, 1259, 773, 1493 cm$^{-1}$; $^1$H NMR (CDCl$_3$) δ2.61, 4.80, 6.70, 6.97, 7.62, 7.95.

Step 2. 2-[[4-(4-Chlorophenyl)-1-piperazinyl]methyl]-8-methylimidazo[1,2-a]pyridine A mixture of 2-(chloromethyl)-8-methylimidazo[1,2-α] pyridine (0.297 g), 1-(4-chlorophenyl) piperazine dihydrochloride (Aldrich; 0.534 g), triethylamine (0.8 mL), THF (6 mL), and DMF (2 mL) is heated at 75° C. for 4 hours. Diisopropylethylamine (0.3 mL) is added and the mixture is stirred another hour, at which time the mixture is concentrated under reduced pressure and the residue is partitioned between saturated aq. sodium bicarbonate and dichloromethane. The organic layers are dried with $MgSO_4$ and concentrated under reduced pressure. The residue is chromatographed on silica gel using methanol/dichloromethane (4/96). The appropriate fractions are combined and concentrated and the residue is crystallized from ethyl acetate/hexane to give 0.231 g of the title compound; mp 102–104° C.; MS m/z 340; IR (mineral oil) 1495, 1338, 2819, 1227, 743 $cm^{-1}$; $^1$H NMR ($CDCl_3$) δ2.61, 2.78, 3.22, 3.85, 6.68, 6.82, 6.94, 7.18, 7.58, 7.95.

EXAMPLE 55

2-[[4-(2,4-Dichlorophenyl)-1-piperazinyl]methyl]-8-methylimidazo[1,2-a]pyridine monomaleic acid salt. Refer to Chart E A mixture of 2-(chloromethyl)-8-methylimidazo[1,2-a]pyridine (Example 54, Step 1; 0.294 g), 1-(2,4-dichlorophenyl)piperazine (Example 31, Step 1; 0.396 g) diisopropylethylamine (0.35 mL), and THF (2 mL) is heated at 75° C. for 5 hours. The mixture is then concentrated under reduced pressure, partitioned between saturated aq. sodium bicarbonate and dichloromethane, and the combined organic layers are dried with $MgSO_4$ and concentrated under reduced pressure. The residue is chromatographed on silica gel using methanol/dichloromethane (4/96) and the appropriate fractions are combined and concentrated to give 2-[[4-(2,4-dichlorophenyl)-1-piperazinyl]methyl]-8-methylimidazo[1,2-a]pyridine. The maleic acid salt is formed by adding maleic acid (0.101 g) to the product dissolved in dichloromethane/methanol. Crystallization from dichloromethane/ether gives 0.2192 g of the title compound; mp 151–152° C.; MS m/z 374, 376; IR (mineral oil) 1482, 1345, 1570, 1357, 867 $cm^{-1}$; $^1$H NMR ($CDCl_3$) δ2.61, 2.80, 3.09, 3.85, 6.67, 6.95, 7.18, 7.35, 7.56, 7.95.

EXAMPLE 56

2-[[4-(4-Chlorophenyl)-1-piperazinyl]methyl]imidazol[1,2-a]pyridine

Following the general procedure of Example 38, Step 2, and making non-critical variations, 2-(chloromethyl)imidazo[1,2-a]pyridine (Example 2, Step 1; 0.25 g) and 1-(4-chlorophenyl)piperazine dihydrochloride (Aldrich; 0.45 g) give 0.25 g of the title compound after chromatography on silica gel using methanol/dichloromethane (4/96), pooling of the appropriate fractions, and crystallization from dichloromethane/ethyl ether; mp 138–139° C.; IR (mineral oil) 1339, 1498, 765, 814, 1223 $cm^{-1}$; $^1$H NMR ($CDCl_3$) δ2.75, 3.20, 3.79, 6.79, 7.17, 7.56, 7.57, 8.08.

EXAMPLE 57

2-[4-[(6-Chloroimidazol[1,2-a]pyridin-2-yl)methyl]-1-piperazinyl]-5-fluorobenazmide Following the general procedure of Example 52 and making non-critical variations, 2-[4-[(6-chloroimidazol[1,2-a]pyridin-2-yl)methyl]-1-piperazinyl]-5-fluorobenzonitrile (Example 21: 0.061 g) is converted to 0.021 g of the title compound after chromatography on silica gel using methanol/dichloromethane (4/96) and crystallization from dichloromethane/hexane; mp 197–198° C. ms m/z at 387, 389; IR (mineral oil) 1669, 1328, 1501, 1428, 825 $cm^{-1}$.

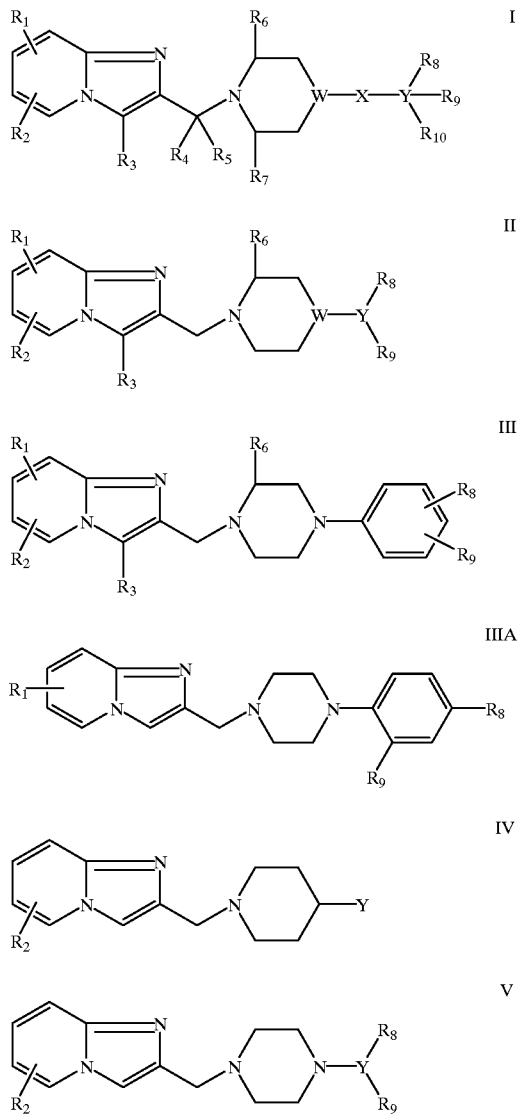

FORMULA CHART

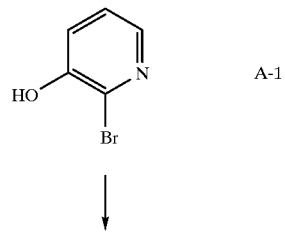

CHART A

-continued
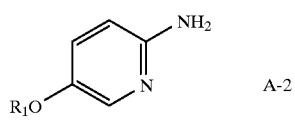  A-2
CHART B
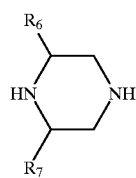 B-a
↓
B-b
↓ (to B-1)
+
B-2
↓
B-3
CHART C
C-1
+
-continued
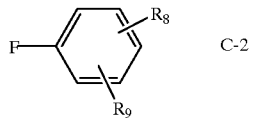  C-2
↓
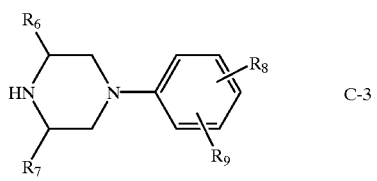  C-3
CHART D
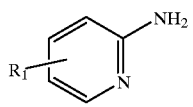  D-1
+
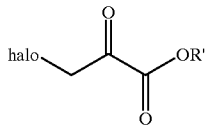  D-2
↓
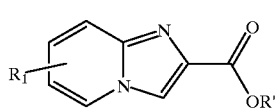  D-3
↓
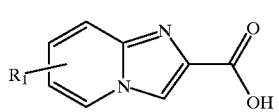  D-4
↓

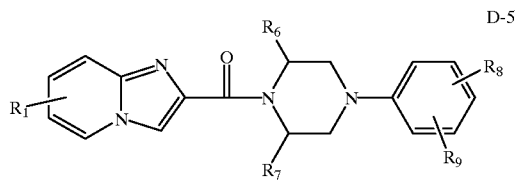
D-5
↓
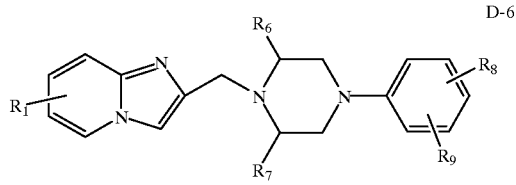
D-6
CHART E
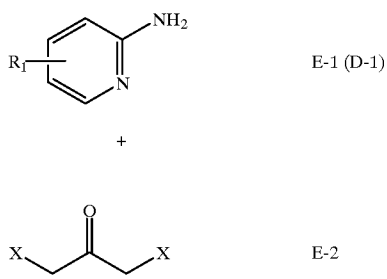
E-1 (D-1)
+
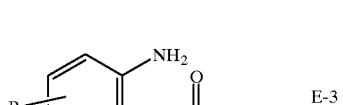
E-2
↓
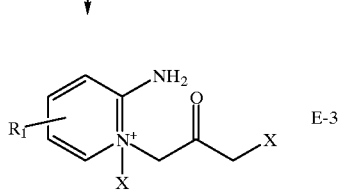
E-3
↓
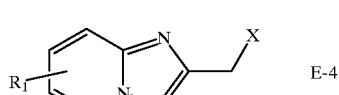
E-4
↓
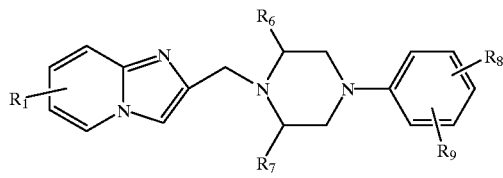
E-5 (D-6)
CHART F
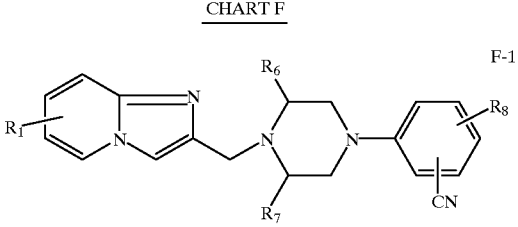
F-1
↓
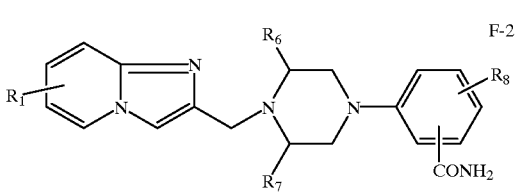
F-2
CHART G
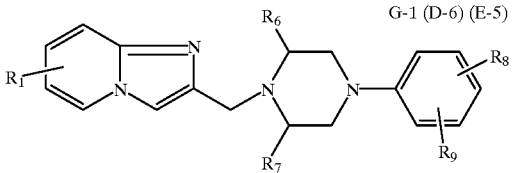
G-1 (D-6) (E-5)
↓
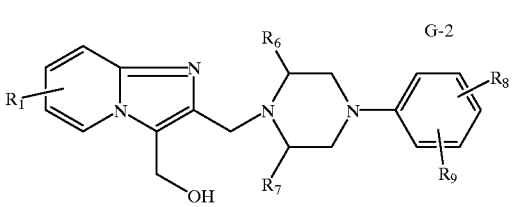
G-2
↓

-continued
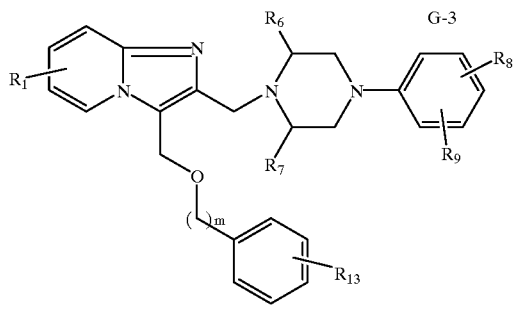
G-3
CHART H
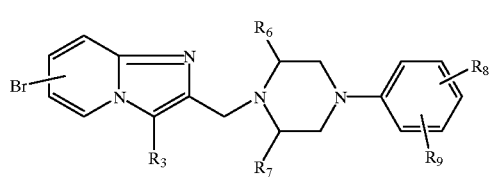
H-1
↓
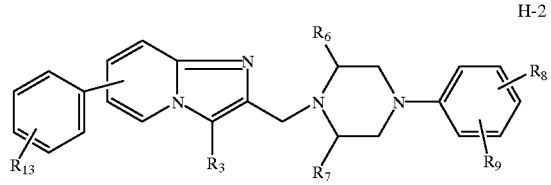
H-2
CHART I
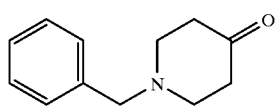
I-1
+
R$_4$NH$_2$  I-2
↓
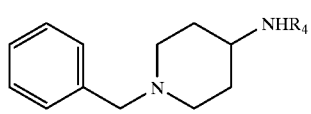
I-3
↓
-continued
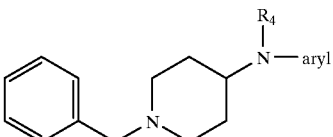
I-4
↓
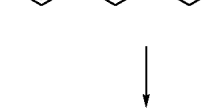
I-5
CHART J
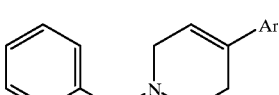
J-1
↓
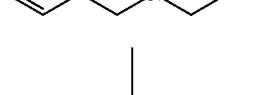
J-2
↓
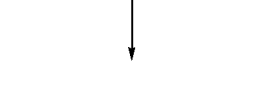
J-3
↓
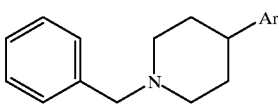
J-4
↓

J-5

CHART K

K-1

↓

K-2

CHART L

E-1

E-2

E-3

E-4

E-5

E-6

E-7

E-8

E-9

E-10

E-11

E-12

E-13

E-14

E-15

E-16

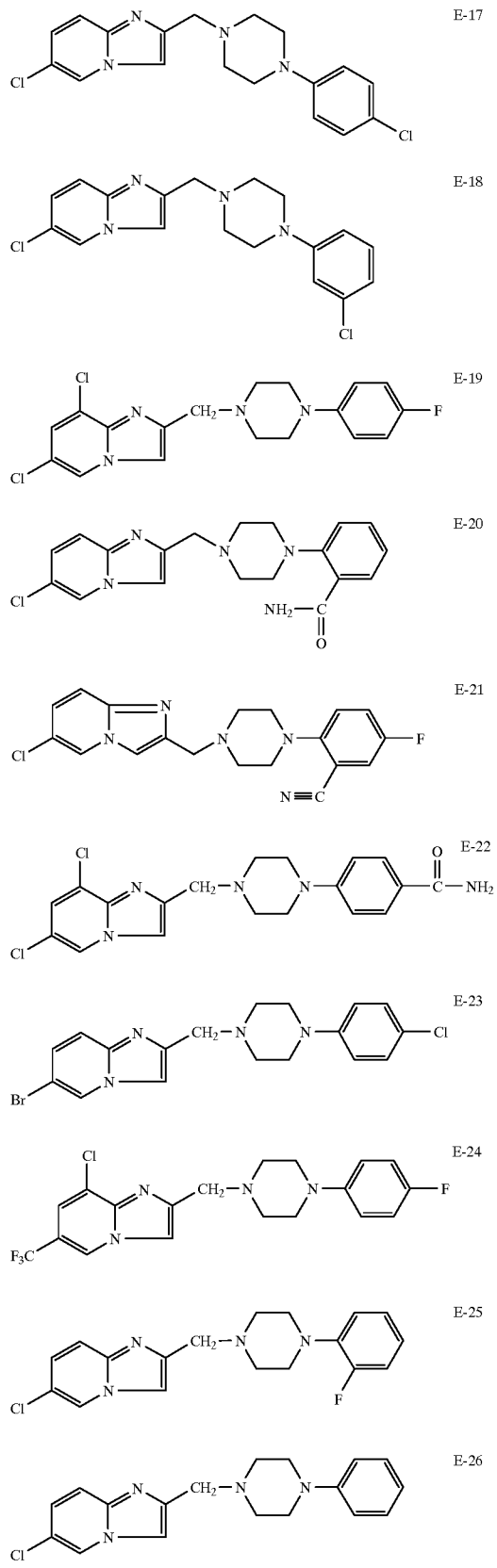
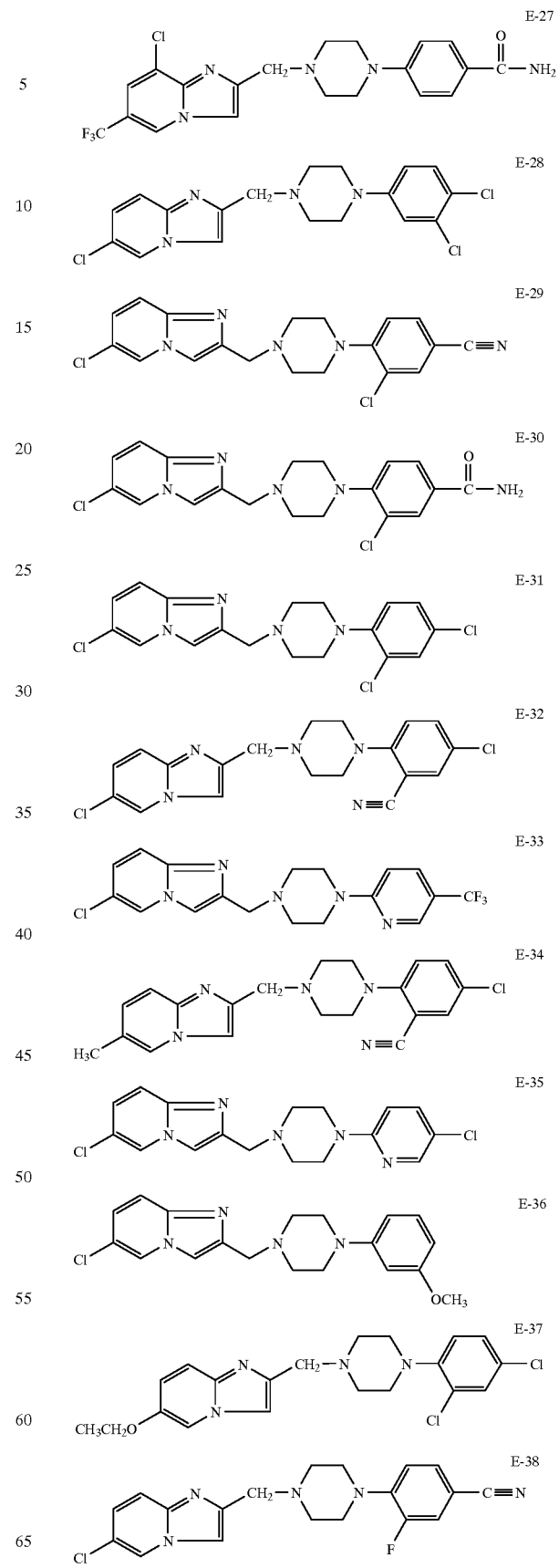

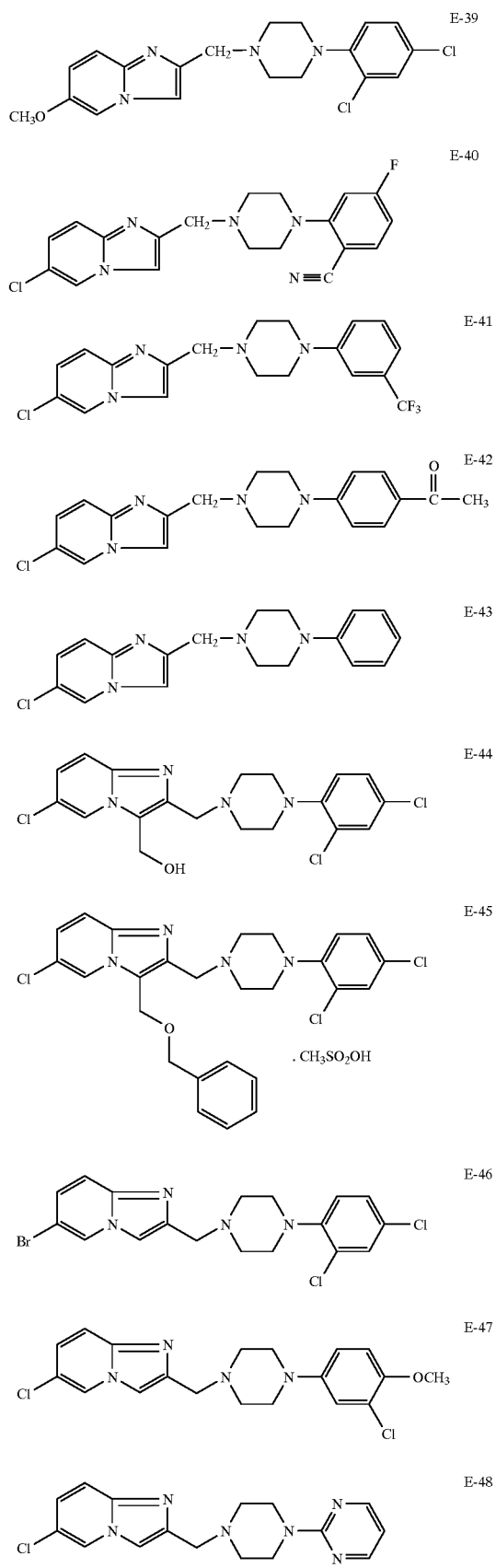

I claim:
1. A compound of the formula I

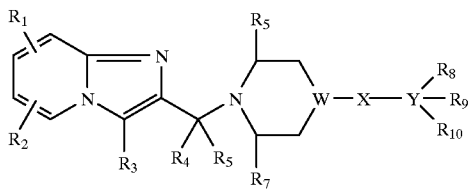

wherein $R_1$ and $R_2$ are the same or different and are
a) H,
b) fluoro,
c) chloro,
d) bromo,
e) iodo,
f) $C_1$–$C_4$ alkyl,
g) $C_3$–$C_7$ cycloalkyl,
h) CN,
i) $CONR_{11}R_{12}$,
j) $SO_2NR_{11}R_{12}$,
k) $NR_{11}R_{12}$,
l) $N(R_{11})SO_2R_{12}$,
m) $N(R_{11})CO(R_{12})$,
n) $NO_2$,
o) OH,
p) $O(C_1$–$C_3$ alkyl),
q) O-phenyl,
r) O—$CF_3$,
s) O—$SO_2CF_3$,
t) SH,
u) $S(C_1$–$C_3$ alkyl),
v) thiazolyl,
w) imidazolyl,
x) oxadiazolyl,
y) aryl optionally substituted with $R_{13}$, or
z) $CF_3$;
wherein $R_3$ is
a) H,
b) halo,
c) CN,
d) OH,
e) $OR_4$,
f) $(CH_2)_nOH$,
g) $(CH_2)_nOR_4$,
h) $(CH_2)_nOCOR_4$,
i) $(CH_2)_nOCOOR_4$,
j) $(CH_2)_nOCONR_{11}R_{12}$,
k) $(CH_2)_nN(R_{11})CONR_{11}R_{12}$,
l) $C_1$–$C_4$ alkyl,
m) $(CH_2)_pCOOR_4$,
n) $(CH_2)_nCONR_{11}R_{12}$,
o) CHO, or
p) $(CH_2)_n$—A—$(CH_2)_m$—Ar$(R_8)(R_9)(R_{10})$;
wherein A is
a) $CH_2$,
b) O,
c) S, or
d) $N(R_{11})$;
wherein $R_4$, $R_5$, $R_6$ and $R_7$ are the same or different and are
a) H,
b) $C_1$–$C_4$ alkyl,
c) $C_3$–$C_7$ cycloalkyl,
d) $C_1$–$C_3$-alkyl-$C_3$–$C_7$ cycloalkyl, or
e) aryl optionally substituted with $R_{13}$;
wherein W is
N;
wherein X is
a) absent, or
b) $N(R_4)$;
wherein Y is
a) phenyl,
b) 2-, 3- or 4-pyridinyl,
c) 2-, 4- or 5-pyrimidinyl,
d) 3- or 4-pyridazinyl,
e) 2-pyrazinyl,
f) 2-, 3-, 6- or 7-imidazo[1,2-a]pyridinyl,
g) 2-benzoxazolyl,
h) 2-thiobenzoxazolyl,
i) 2-thiazolyl,
j) 1,3-dihydro-2H-benzimidazol-2-onyl, or
k) 1,3-dihydro-3-methyl-2H-benzimidazol-2-onyl;
wherein $R_8$, $R_9$ and $R_{10}$ are the same or different and are
a) hydrogen,
b) fluoro,
c) chloro,
d) bromo,
e) iodo,
f) $C_1$–$C_4$ alkyl,
g) $C_3$–$C_7$ cycloalkyl,
h) CN,
i) $CONR_{11}R_{12}$
j) $SO_2NR_{11}R_{12}$,
k) $NR_{11}R_{12}$,
l) $N(R_{11})SO_2R_{12}$,
m) $N(R_{11})COR_{12}$,
n) $NO_2$,
o) OH,
p) $O(C_1$–$C_3$ alkyl),
q) O-aryl optionally substituted with $R_{13}$,
r) O—$CF_3$,
s) O—$SO_2CF_3$,
t) SH,
u) $S(C_1$–$C_3$ alkyl),
v) thiazolyl,
w) imidazolyl,
x) oxadiazolyl,
y) phenyl, or
z) 2-, 3- or 4-pyridinyl;
a1) $CF_3$,
b1) —$C(O)C_1$–$C_4$alkyl,
c1) $C(O)OR_4$, or
d1) $SO_2$-phenyl optionally substituted with $R_{13}$;

wherein $R_{11}$ and $R_{12}$ are the same or different and are
a) H,
b) $C_1$–$C_4$ alkyl,
c) $C_3$–$C_7$ cycloalkyl,
d) $C_1$–$C_3$ alkyl-$C_3$–$C_7$ cycloalkyl, or
e) aryl optionally substituted with $R_{13}$;
when $R_{11}$ and $R_{12}$ occur in $NR_{11}R_{12}$, $R_{11}$ and $R_{12}$ may be taken together with a methylene group or a heteroatom to form piperazine, morpholine, thiomorpholine, piperidine, or pyrrolidine;
wherein aryl is
a) phenyl,
b) naphthyl,
c) 2-, 3- or 4-pyridinyl, or
d) 2-, 4- or 5-pyrimidinyl;
wherein $R_{13}$ is
a) H,
b) fluoro,
c) chloro,
d) bromo,
e) iodo,
f) $CH_3$,
g) $CF_3$,
h) CN,
i) OH, or
j) $OCH_3$;
wherein n is one (1) to four (4) inclusive;
wherein m is zero (0) to four (4) inclusive;
wherein p is two (2) to four (4) inclusive;
or pharmaceutically acceptable salts or enantiomers diastereomers thereof; with the following provisos:

1) when $R_1$ or $R_2$ is —$CONR_{11}R_{12}$, then $R_{11}$ and $R_{12}$ are not both H; and
2) when $R_8$, $R_9$ or $R_{10}$ is —$CONR_{11}R_{12}$ wherein $R_{11}$ and $R_{12}$ are both H.

then X is absent.

2. The compound of claim 1 of the formula II

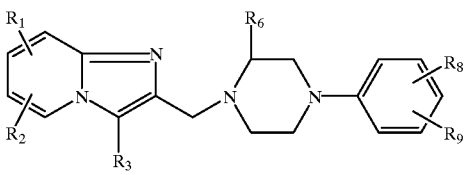

wherein $R_1$ and $R_2$ are the same or different and are
a) H,
b) chloro,
c) bromo,
d) $CH_3$
e) $O(C_1$–$C_2$ alkyl),
f) phenyl, or
g) $CF_3$;
wherein $R_3$ is
a) H,
b) $(CH_2)OH$, or
c) $CH_2$—O—$CH_2$-phenyl;
wherein $R_6$ is
a) H, or
b) $CH_3$;
wherein W is
N;
wherein Y is
a) phenyl,
b) 2-pyridinyl,
c) 2-pyrimidinyl,
d) 1,3-dihydro-2H-benzimidazol-2-one, or
e) 1,3-dihydro-3-methyl-2H-benzimidazol-2-one;
wherein $R_8$ and $R_9$ are the same or different and are
a) hydrogen,
b) fluoro,
c) chloro,
d) CN,
e) $CONH_2$,
f) $OCH_3$,
g) $CF_3$,
h) $C(O)CH_3$, or
i) $SO_2NH_2$;
or pharmaceutically acceptable salt or enantiomers or diastereomers thereof.

3. The compound of claim 2 of the formula III

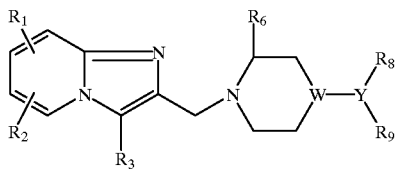

wherein $R_1$ and $R_2$ are the same or different and are
a) H,
b) chloro,
c) bromo,
d) $CH_3$,
e) $OCH_3$,
f) $OCH_2CH_2$,
g) phenyl, or
h) $CF_3$;
wherein $R_3$ is
a) H,
b) $CH_2OH$,
c) $CH_2$—O—$CH_2$-phenyl;
wherein $R_6$ is
a) H, or
b) $CH_3$;
wherein $R_8$ and $R_9$ are the same or different and are:
a) hydrogen,
b) fluoro,
c) chloro,
d) CN,
e) $CONH_2$,
f) $OCH_3$,
g) $CF_3$,
h) $C(O)CH_3$, or
i) $SO_2NH_2$;
or pharmaceutically acceptable salts or enantiomers or diastereomers thereof.

4. The compound of claim 3 of the formula IIIA

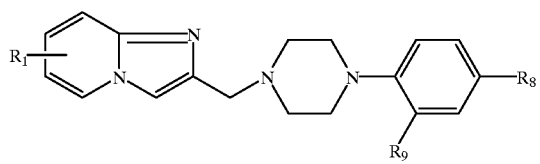

IIIA wherein R₁ is
a) H,
b) bromo,
c) chloro, or
d) CH₃;
wherein R₈ and R₉ are the same or different and are
a) H or
b) chloro;
or pharmaceutically acceptable salts or enantiomers or diastereomers thereof.

5. The compound of claim 2 of the formula V

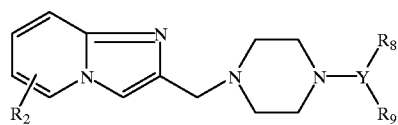

V wherein R₂ is chloro;
wherein Y is
a) 2-pyridinyl, or
b) 2-pyrimidinyl;
wherein R₈ and R₉ are the same or different and are
a) H,
b) Cl, or
c) CF₃;
or pharmaceutically acceptable salt or enantiomers or diastereomers thereof.

6. The compound of claim 2 selected from the group consisting of:
6Chloro-2-[[4-(4-methoxyphenyl)-1-piperazinyl]methyl]imidazo[1,2-a]pyridine;
4-[4-[(Imidazo[1,2-a]pyridin-2-yl)methyl]-1-piperazinyl]benzenesulfonamide;
4-[4-[(Imidazo[1,2-a]pyridin-2-yl)methyl]-1-piperazinyl]benzamide;
4-[4-[(6-Chloroimidazo[1,2-a]pyridin-2-yl)methyl]-1-piperazinyl]benzamide;
4-[4-[(6-Chloroimidazo[1,2-a]pyridin-2-yl)methyl]-1-piperazinyl]benzenesulfonamide;
2-[[4-(4-Fluorophenyl)-1-piperazinyl]methyl]-7-methylimidazo[1,2-a]pyridine;
4-[4-[(7-Methylimidazo[1,2-a]pyridin-2-yl)methyl]-1-piperazinyl]benzamide;
2-[[4-(4-Fluorophenyl)-1-piperazinyl]methyl]-6-methylimidazo[1,2-a]pyridine;
4-[4-[(6-Methylimidazo[1,2-a]pyridin-2-yl)methyl]-1-piperazinyl]benzamide;
6-Chloro-2-[[4-(4-fluorophenyl)-1-piperazinyl]methyl]imidazo[1,2-a]pyridine;
6-Chloro-2-[[4-(2-chlorophenyl)-1-piperazinyl]methyl]imidazo[1,2-a]pyridine;
2-[4[[(6-Chloroimidazo [1,2-a]pyridin-2-yl)methyl]-1-piperazinyl]benzonitrile;
6-Bromo-2-[[4-(4-fluorophenyl)-1-piperazinyl]methyl]imidazo[1,2-a]pyridine;
4-[4-[(6-Bromoimidazo[1,2-a]pyridin-2-yl)methyl]-1-piperazinyl]benzamide;
6-Chloro-2-[[4-(4-chlorophenyl)-1-piperazinyl]methyl]imidazo[1,2-a]pyridine;
6-Chloro-2-[[4-(3-chlorophenyl)-1-piperazinyl]methyl]imidazo[1,2-a]pyridine;
6,8-Dichloro-2-[[4-(4-fluorophenyl)-1-piperazinyl]methyl]imidazo[1,2-a]pyridine;
2-[4-[(6-Chloroimidazo[1,2-a]pyridin-2-yl)methyl]-1-piperazinyl]benzamide;
2-[4-[(6-Chloroimidazo[1,2-a]pyridin-2-yl)methyl]-1-piperazinyl]-5-fluorobenzonitrile;
4-[4-[(6,8-Dichloroimidazo[1,2-a]pyridin-2-yl )methyl]-1-piperazinyl]benzamide;
6-Bromo-2-[[4-(4-chlorophenyl)-1-piperazinyl]methyl]imidazo[1,2-a]pyridine;
8-Chloro-2-[[4-(4-fluorophenyl)-1-piperazinyl]methyl]-6-trifluoromethylimidazo[1,2-a]pyridine;
6-Chloro-2-[[4-(2-fluorophenyl)-1-piperazinyl]methyl]imidazo[1,2-a]pyridine;
6-Chloro-2-[(4-phenyl-1-piperazinyl)methyl]imidazo[1,2-a]pyridine;
4-[4-[(8-Chloro-6-trifluoromethylimidazo[1,2-a]pyridin-2-yl)methyl]-1-piperazinyl]benzamide;
6-Chloro-2-[[4-(3,4-dichlorophenyl)-1-piperazinyl]methyl]imidazo[1,2-a]pyridine;
3-Chloro-4-[4-[(6-chloroimidazo[1,2-a]pyridin-2-yl)methyl]-1-piperazinyl]benzonitrile;
3-Chloro4-[4-[(6-chloroimidazo[1,2-a]pyridin-2-yl)methyl]-1-piperazinyl]benzamide;
6-Chloro-2-[[4-(2,4-dichlorophenyl)-1-piperazinyl]methyl]imidazo(1,2-a]pyridine;
5-Chloro-2-[4-[(6-chloroimidazo[1,2-a]pyridin-2-yl)methyl]-1-piperazinyl]benzonitrile;
6-Chloro-2-[[4-[5-(trifluoromethyl)pyridin-2-yl]-1-piperazinyl]methyl]imidazo[1,2-a]pyridine;
5-Chloro-2-[4-[(6-methylimidazo[1,2-a]pyridin-2-yl)methyl]-1-piperazinyl]benzonitrile;
6-Chloro-2-[[4-(5-chloropyridin-2-yl)-1-piperazinyl]methyl]imidazo[1,2-a]pyridine;
6-Chloro-2-[[4-(3-methoxyphenyl)-1-piperazinyl]methyl]imidazo[1,2-a]pyridine;
2-[[4-(2,4-Dichlorophenyl)-1-piperazinyl]methyl]-6-ethoxyimidazo[1,2-a]pyridine;
4-[4-[(6-Chloroimidazo[1,2-a]pyridin-2-yl)methyl]-1-piperazinyl]-3-fluorobenzonitrile;
2-[[4-(2,4-Dichlorophenyl)-1-piperazinyl]methyl]-6-methoxyimidazo[1,2-a]pyridine;
2-[4-[(6-Chloroimidazo[1,2-a]pyridin-2-yl)methyl]-1-piperazinyl]-4-fluorobenzonitrile;
6-Chloro-2-[[4-[3-(trifluoromethyl)phenyl]-1-piperazinyl]methyl]imidazo[1,2-a]pyridine:
1-[4-[4-[(6-Chloroimidazo[1,2-a]pyridin-2-yl)methyl]-1-piperazinyl]phenyl]ethanone;
6-Chloro-2-[[4-(2,4-dichlorophenyl)-1-piperazinyl]methyl]imidazo[1,2-a]pyridine-3-methanol;
6-Chloro-2-[[4-(2,4-dichlorophenyl)-1-piperazinyl]methyl]-3-[(phenylmethoxy)methyl]imidazo[1,2-a]pyridine monomethanesulfonate;

6-Bromo-2-[[4-(2,4-dichlorophenyl)-1-piperazinyl]
methyl]imidazo[1,2-a]pyridine;

6-Chloro-2-[[4-(3-chloro-4-methoxyphenyl)-1-
piperazinyl]methyl]imidazo[1,2-a]pyridine;

6-Chloro-2-[[4-(2-pyrimidinyl)-1-piperazinyl]methyl]
imidazo[1,2-a]pyridine;

2-[[4-(2,4-Dichlorophenyl)-1-piperazinyl]methyl]-6-
(trifluoromethyl)imidazo[1,2-a]pyridine;
monomethanesulfonate 2-[[4-(4-Chlorophenyl)-1-piperazinyl]methyl]-6-
(trifluoromethyl)imidazo[1,2-a]pyridine;

2-[[4-(4-Chlorophenyl)-1-piperazinyl]methyl]-6-
phenylimidazo[1,2-a]pyridine;

4-[4-[(6-Chloroimidazo[1,2-a]pyridin-2-yl)methyl]-1-
piperazinyl]-3-fluorobenzamide;

(RS)-4-[4-[(6-Chloroimidazo[1,2-a]pyridin-2-yl)
methyl]-3-methylpiperazin-1-yl]benzamide;

2-[[4-(4-Chlorophenyl)-1-piperazinyl]methyl]-8-
methylimidazo[1,2-a]pyridine;

2-[[4-(2,4-Dichlorophenyl)-1-piperazinyl]methyl]-8-
methylimidazo(1,2-a]pyridine monomaleic acid salt;

2-[[4-(4-Chlorophenyl)-1-piperazinyl]methyl]imidazol
[1,2-a]pyridine; and

2-[4-[(6-Chloroimidazol[1,2-a]pyridin-2-yl)methyl]-1-
piperazinyl]-5-fluorobenazmide.

7. The compound of claim 4 selected from the group consisting of:

6-Bromo-2-[[4-(4-chlorophenyl)-1-piperazinyl]methyl]
imidazo[1,2-a]pyridine;

6-Chloro-2-[[4-(2,4-dichlorophenyl)-1-piperazinyl]
methyl]imidazo[1,2-a]pyridine;

2-[[4-(4-Chlorophenyl)-1-piperazinyl]methyl]-8-
methylimidazo[1,2-a]pyridine;

2-[[4-(2,4-Dichlorophenyl)-1-piperazinyl]methyl]-8-
methylimidazo[1,2-a]pyridine monomaleic acid salt; and 2-[[4-(4-Chlorophenyl)-1-piperazinyl]methyl]imidazol
[1,2-a]pyridine.

8. A method for treating a patient having schizophrenia or psychosis which comprises:

administering an effective amount of a compound of formula I of claim 1.

9. The method of claim 8 wherein the compound is selected from the group consisting of:

6-Chloro-2-[[4-(4-methoxyphenyl)-1-piperazinyl]
methyl]imidazo[1,2-a]pyridine;

4-[4-[(Imidazo[1,2-a]pyridin-2-yl)methyl]-1-piperazinyl]
benzenesulfonamide;

4-[4-[(Imidazo[1,2-a]pyridin-2-yl)methyl]-1-piperazinyl]
benzamide;

4-[4-[(6-Chloroimidazo[1,2-a]pyridin-2-yl)methyl]-1-
piperazinyl]benzamide;

4-[4-[(6-Chloroimidazo[1,2-a]pyridin-2-yl)methyl]-1-
piperazinyl]benzenesulfonamide;

2-[[4-(4-Fluorophenyl)-1-piperazinyl]methyl]-7-
methylimidazo[1,2-a]pyridine;

4-[4-[(7-Methylimidazo[1,2-a]pyridin-2-yl)methyl]-1-
piperazinyl]benzamide;

2-[[4-(4-Fluorophenyl)-1-piperazinyl]methyl]-6-
methylimidazo[1,2-a]pyridine;

4-[4-[(6-Methylimidazo[1,2-a]pyridin-2-yl)methyl]-1-
piperazinyl]benzamide;

6-Chloro-2-[[4-(4-fluorophenyl)-1-piperazinyl]methyl]
imidazo[1,2-a]pyridine;

6-Chloro-2-[[4-(2-chlorophenyl)-1-piperazinyl]methyl]
imidazo[1,2-a]pyridine;

2-[4-[(6-Chloroimidazo[1,2-a]pyridin-2-yl)methyl]-1-
piperazinyl]benzonitrile;

6-Bromo-2-[[4-(4-fluorophenyl)-1-piperazinyl]methyl]
imidazo[1,2-a]pyridine;

4-[4-[(6-Bromoimidazo[1,2-a]pyridin-2-yl)methyl]-1-
piperazinyl]benzamide;

6-Chloro-2-[[4-(4-chlorophenyl)-1-piperazinyl]methyl]
imidazo[1,2-a]pyridine;

6-Chloro-2-[[4-(3-chlorophenyl)-1-piperazinyl]methyl]
imidazo[1,2-a]pyridine;

6,8-Dichloro-2-[[4-(4-fluorophenyl)-1-piperazinyl]
methyl]imidazo[1,2-a]pyridine;

2-[4-[(6-Chloroimidazo[1,2-a]pyridin-2-yl)methyl]-1-
piperazinyl]benzamide;

2-[4-[(6-Chloroimidazo[1,2-a]pyridin-2-yl)methyl]-1-
piperazinyl]-5-fluorobenzonitrile;

4-[4-[(6,8-Dichloroimidazo[1,2-a]pyridin-2-yl)methyl]-
1-piperazinyl]benzamide;

6-Bromo-2-[[4-(4-chlorophenyl)-1-piperazinyl]methyl]
imidazo[1,2-a]pyridine;

8-Chloro-2-[[4-(4-fluorophenyl)-1-piperazinyl]methyl]-
6-trifluoromethylimidazo[1,2-a]pyridine;

6-Chloro-2-[[4-(2-fluorophenyl)-1-piperazinyl]methyl]
imidazo[1,2-a]pyridine;

6-Chloro-2-[(4-phenyl-1-piperazinyl)methyl]imidazo[1,
2-a]pyridine;

4-[4-[(8-Chloro-6-trifluoromethylimidazo[1,2-a]pyridin-
2-yl)methyl]-1-piperazinyl]benzamide;

6-Chloro-2-[[4-(3,4-dichlorophenyl)-1-piperazinyl]
methyl]imidazo[1,2-a]pyridine;

3-Chloro-4-[4-[(6-chloroimidazo[1,2-a]pyridin-2-yl)
methyl]-1-piperazinyl]benzonitrile;

3-Chloro4-[4-[(6-chloroimidazo[1,2-a]pyridin-2-yl)
methyl]-1-piperazinyl]benzamide;

6-Chloro-2-[[4-(2,4-dichlorophenyl)-1-piperazinyl]
methyl]imidazo[1,2-a]pyridine;

5-Chloro-2-[4-[(6-chloroimidazo[1,2-a]pyridin-2-yl)
methyl]-1-piperazinyl]benzonitrile;

6-Chloro-2-[[4-[5-(trifluoromethyl)pyridin-2-yl]-1-
piperazinyl]methyl]imidazo[1,2-a]pyridine;

5-Chloro-2-[4-[(6-methylimidazo[1,2-a]pyridin-2-yl)
methyl]1-piperazinyl]benzonitrile;

6-Chloro-2-[[4-(5-chloropyridin-2-yl)-1-piperazinyl]
methyl]imidazo[1,2-a]pyridine;

6-Chloro-2-[[4-(3-methoxyphenyl)-1-piperazinyl]
methyl]imidazo[1,2-a]pyridine;

2-[[4-(2,4-Dichlorophenyl)-1-piperazinyl]methyl]-6-
ethoxyimidazo[1,2-a]pyridine;

4-[4-[(6-Chloroimidazo[1,2-a]pyridin-2-yl)methyl]-1-
piperazinyl]-3-fluorobenzonitrile;

2-[[4-(2,4-Dichlorophenyl)-1-piperazinyl]methyl]-6-
methoxyimidazo[1,2-a]pyridine;

2-[4-[(6-Chloroimidazo[1,2-a]pyridin-2-yl)methyl]-1-
piperazinyl]-4-fluorobenzonitrile;

6-Chloro-2-[[4-[3-(trifluoromethyl)phenyl]-1-
piperazinyl]methyl]imidazo[1,2-a]pyridine;

1-[4-[4-[(6-Chloroimidazo[1,2-a]pyridin-2-yl)methyl]-1-
piperazinyl]phenyl]ethanone;

6-Chloro-2-[[4-(2,4-dichlorophenyl)-1-piperazinyl]methyl]imidazo[1,2-a]pyridine-3-methanol;

6-Chloro-2-[[4-(2,4-dichlorophenyl)-1-piperazinyl]methyl]-3-[(phenylmethoxy)methyl]imidazo[1,2-a]pyridine monomethanesulfonate;

6-Bromo-2-[[4-(2,4-dichlorophenyl)-1-piperazinyl]methyl]imidazo[1,2-a]pyridine;

6-Chloro-2-[[4-(3-chloro-4-methoxyphenyl)-1-piperazinyl]methyl]imidazo[1,2-a]pyridine;

6-Chloro-2-[[4-(2-pyrimidinyl)-1-piperazinyl]methyl]imidazo[1,2-a]pyridine;

2-[[4-(2,4-Dichlorophenyl)-1-piperazinyl]methyl]-6-(trifluoromethyl)imidazo[1,2-a]pyridine; monomethanesulfonate 2-[[4-(4-Chlorophenyl)-1-piperazinyl]methyl]-6-(trifluoromethyl)imidazo[1,2-a]pyridine;

2-[[4-(4-Chlorophenyl)-1-piperazinyl]methyl]-6-phenylimidazo[1,2-a]pyridine;

4-[4-[(6-Chloroimidazo[1,2-a]pyridin-2-yl)methyl]-1-piperazinyl]-3-fluorobenzamide;

(RS)-4-[4-[(6-Chloroimidazo[1,2-a]pyridin-2-yl)methyl]-3-methylpiperazin-1-yl]benzamide;

2-[[4-(4-Chlorophenyl)-1-piperazinyl]methyl]-8-methylimidazo[1,2-a]pyridine;

2-[[4-(2,4-Dichlorophenyl)-1-piperazinyl]methyl]-8-methylimidazo[1,2-a]pyridine monomaleic acid salt;

2-[[4-(4-Chlorophenyl)-1-piperazinyl]methyl]imidazol[1,2-a]pyridine; and

2-[4-[(6-Chloroimidazol[1,2-a]pyridin-2-yl)methyl]-1-piperazinyl]-5-fluorobenzamide.

10. The method of claim 9 wherein the compound is selected from the group consisting of:

6-Bromo-2-[[4-(4-chlorophenyl)-1-piperazinyl]methyl]imidazo[1,2-a]pyridine;

6-Chloro-2-[[4-(2,4-dichlorophenyl)-1-piperazinyl]methyl]imidazo[1,2-a]pyridine;

2-[[4-(4-Chlorophenyl)-1-piperazinyl]methyl]-8-methylimidazo[1,2-a]pyridine;

2-[[4-(2,4-Dichlorophenyl)-1-piperazinyl]methyl]-8-methylimidazo[1,2-a]pyridine monomaleic acid salt; and 2-[[4-(4-Chlorophenyl)-1-piperazinyl]methyl]imidazol[1,2-a]pyridine.

* * * * *